(12) United States Patent
Maruyama et al.

(10) Patent No.: US 10,709,590 B2
(45) Date of Patent: Jul. 14, 2020

(54) MANUFACTURING METHOD OF STENT AND COATING DEVICE

(71) Applicant: Terumo Kabushiki Kaisha, Shibuya-ku, Tokyo (JP)

(72) Inventors: Kazuhiro Maruyama, Hiratsuka (JP); Yasuyuki Kuroda, Fujinomiya (JP); Masaki Watanabe, Fuji (JP); Kazuyuki Takeda, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 15/070,270

(22) Filed: Mar. 15, 2016

(65) Prior Publication Data

US 2016/0235565 A1    Aug. 18, 2016

Related U.S. Application Data

(63) Continuation of application No. PCT/JP2014/075130, filed on Sep. 22, 2014.

(30) Foreign Application Priority Data

Sep. 27, 2013    (JP) ................................ 2013-200840

(51) Int. Cl.
*A61F 2/91*    (2013.01)
*B05B 14/00*    (2018.01)
(Continued)

(52) U.S. Cl.
CPC ............... *A61F 2/91* (2013.01); *B05B 14/00* (2018.02); *B05B 15/52* (2018.02); *B05C 5/0216* (2013.01);
(Continued)

(58) Field of Classification Search
CPC .................................................... B05C 5/0216
(Continued)

(56) References Cited

U.S. PATENT DOCUMENTS 6,395,326 B1 *    5/2002    Castro .................... A61L 31/10
                                                                                427/2.24
9,072,622 B2    7/2015    Kindaichi et al.
(Continued)

FOREIGN PATENT DOCUMENTS

CN    101045228 A    10/2007
CN    101616644 A    12/2009
(Continued)

OTHER PUBLICATIONS

Extended European Search Report dated Mar. 15, 2017, issued by the European Patent Office in corresponding European Application No. EP 14846854.9 (12 pages).
(Continued)

*Primary Examiner* — Cachet I Proctor
(74) *Attorney, Agent, or Firm* — Buchanan Ingersoll & Rooney PC

(57) ABSTRACT

A manufacturing method of a stent is disclosed which prevents a drug from being peeled off or separated due to stress concentration or distortion resulting from the expanding deformation of the stent so that the drug is further uniformly effective and further improved yields are expected when the stent is manufactured, and a coating device. The method has a non-coating portion forming process of preventing a bending portion from being coated with the drug by causing a nozzle to go past the bending portion when the nozzle reaches the bending portion and to move toward main strut portions. In the non-coating portion forming process, an adhesion amount of a coating solution is reduced while the nozzle is going past the bending portion.

20 Claims, 17 Drawing Sheets

(51) Int. Cl.
  *B05B 15/52* (2018.01)
  *B05C 5/02* (2006.01)
  *B05C 11/10* (2006.01)
  *B05C 13/02* (2006.01)
  *B05D 1/26* (2006.01)
  *B05D 1/02* (2006.01)

(52) U.S. Cl.
  CPC ........ *B05C 5/0225* (2013.01); *B05C 11/1021* (2013.01); *B05C 13/02* (2013.01); *B05D 1/26* (2013.01); *A61F 2240/001* (2013.01); *A61F 2250/0067* (2013.01); *B05D 1/02* (2013.01)

(58) Field of Classification Search
  USPC .............................................. 427/2.24, 2.25
  See application file for complete search history.

(56) References Cited

U.S. PATENT DOCUMENTS

| | | | |
|---|---|---|---|
| 9,750,853 B2* | 9/2017 | Huang | A61L 31/10 |
| 2003/0083646 A1 | 5/2003 | Sirhan et al. | |
| 2003/0088307 A1* | 5/2003 | Shulze | A61F 2/91 |
| | | | 623/1.15 |
| 2004/0247775 A1* | 12/2004 | Boulais | B05C 5/0216 |
| | | | 427/2.1 |
| 2007/0116856 A1* | 5/2007 | Hossainy | A61F 2/91 |
| | | | 427/2.24 |
| 2008/0003349 A1* | 1/2008 | Van Sciver | B05B 13/0235 |
| | | | 427/8 |
| 2008/0311280 A1* | 12/2008 | Rego | B05D 1/02 |
| | | | 427/2.24 |
| 2008/0311281 A1 | 12/2008 | Andreacchi et al. | |
| 2009/0232964 A1* | 9/2009 | Chen | A61L 31/10 |
| | | | 427/2.25 |
| 2009/0234432 A1* | 9/2009 | Pacetti | A61F 2/91 |
| | | | 623/1.16 |
| 2010/0034960 A1* | 2/2010 | Kindaichi | A61F 2/91 |
| | | | 427/2.25 |
| 2010/0262230 A1* | 10/2010 | Vecerina | B05B 12/122 |
| | | | 623/1.46 |
| 2011/0000427 A1* | 1/2011 | Bobson | F26B 21/004 |
| | | | 118/64 |
| 2012/0076949 A1 | 3/2012 | Iwashima et al. | |
| 2012/0165923 A1* | 6/2012 | Maruyama | A61F 2/915 |
| | | | 623/1.42 |
| 2012/0171353 A1 | 7/2012 | Walsh | |

FOREIGN PATENT DOCUMENTS

| | | |
|---|---|---|
| CN | 102416761 A | 4/2012 |
| CN | 102448406 A | 5/2012 |
| EP | 2 127 617 A1 | 12/2009 |
| EP | 2 444 034 A1 | 4/2012 |
| EP | 2 526 902 A1 | 11/2012 |
| JP | 2005-508671 A | 4/2005 |
| JP | 2007-525312 A | 9/2007 |
| JP | 2009-542318 A | 12/2009 |
| JP | 2010-529886 A | 9/2010 |
| JP | 2011-502723 A | 1/2011 |
| WO | 03/009779 A2 | 2/2003 |
| WO | WO 2009-065087 A1 | 5/2009 |
| WO | WO 2011/040218 A1 | 4/2011 |

OTHER PUBLICATIONS

International Search Report (PCT/ISA/210) dated Dec. 22, 2014, by the Japanese Patent Office as the International Searching Authority for International Application No. PCT/JP2014/075130.
Written Opinion (PCT/ISA/237) dated Dec. 22, 2014, by the Japanese Patent Office as the International Searching Authority for International Application No. PCT/JP2014/075130.
Notification of First Office Action dated Dec. 26, 2016 by the State Intellectual Property Office of the People's Republic of China in corresponding Chinese Application No. 201480053338.1 (24 pages).
English translation of the Second Office Action dated Jun. 28, 2017 in corresponding Chinese Patent Application No. 201480053338.1.
Notification of Reasons for Refusal dated Oct. 17, 2017, in corresponding Japanese Patent Application No. 2015-539216, and an English translation thereof.
Decision of Refusal dated Feb. 13, 2018, in corresponding Japanese patent Application No. 2015-539216, and an English translation thereof.
Office Action dated Jul. 2, 2018 issued in corresponding European Patent Application No. 14 846 854.9.

* cited by examiner

MANUFACTURING METHOD OF STENT AND COATING DEVICE

CROSS-REFERENCES TO RELATED APPLICATIONS

This application is a continuation of International Application No. PCT/JP2014/075130 filed on Sep. 22, 2014, and claims priority to Japanese Application No. 2013-200840 filed on Sep. 27, 2013, the entire content of both of which is incorporated herein by reference.

TECHNICAL FIELD

The present disclosure generally relates to a manufacturing method of a stent, and a coating device.

BACKGROUND DISCUSSION

A stent is a medical device including a mesh-like cylindrical body in which multiple annular bodies configured to include waved struts having a bending portion are arranged in an axial direction so that the adjacent annular bodies are integrated with each other via a link portion. For example, the stent is applied in order to prevent a restenosis after percutaneous transluminal coronary angioplasty (PTCA) or percutaneous coronary intervention (PCI) which is used in treating myocardial infarction or angina pectoris.

In a case where a so-called bare metal stent which is not coated with a drug is applied, a restenosis rate can be lower than that in a case of the PTCA or the PCI without using the stent at all. However, it has been recognized that restenosis occurs in a stent indwelling portion at a rate of approximately 20% to 30%. A major factor of restenosis is intimal hypertrophy caused by the migration and proliferation of vascular smooth muscle cells. Therefore, drug eluting stents (DES) have been developed which help prevent the restenosis by coating an outer surface of the stent with a drug for inhibiting the migration and proliferation of vascular smooth muscle cells and by eluting the drug in a stent indwelling portion.

For example, as disclosed in JP-T-2011-502723, the drug coating is performed in such a way that a coating solution prepared by dissolving the drug and a biocompatible polymer into a solvent is discharged along an outer surface of a strut by using a spray nozzle, and thereafter, is dried and solidified.

In general, the stent is expanded and deformed when the stent indwells after reaching a target portion inside a lumen. Therefore, due to the expanding deformation, stress concentration and/or distortion occurs in a drug coating layer formed on an outer surface of a bending portion of the strut. Consequently, there is a problem in that the drug coating layer is peeled off or separated therefrom.

In order to solve this problem, a stent disclosed in pamphlet of International Publication No. 2011/040218 employs a bending portion serving as a non-coating layer which is not coated with a drug, thereby preventing a coating layer from being peeled off and separated. In addition, as a method of forming the non-coating layer, when a nozzle for discharging the drug reaches the bending portion, the nozzle is caused to perform separating movement (jumping) from the bending portion, thereby preventing the bending portion from being coated with the drug.

In a case where the above-described method is employed, although the bending portion can be suitably prevented from being coated with the drug, the nozzle inevitably stores the drug while the nozzle performs the separating movement. Consequently, the drug is excessively discharged immediately after the nozzle passes through the bending portion. For example, in some cases, not only an outer surface which is initially supposed to be coated but also a side surface portion is coated with the drug. Consequently, there is a possibility that the drug may no longer be uniformly effective, or that poor yields may be expected when the stent is manufactured.

SUMMARY

A manufacturing method of a stent is disclosed, which helps prevent a drug from being peeled off or separated due to stress concentration or distortion resulting from the expanding deformation of the stent so that the drug is further uniformly effective and further improved yields are expected when the stent is manufactured, and to provide a coating device.

A manufacturing method of a stent is disclosed that has an annular body configured to include a waved strut which at least has first and second main strut portions to be coated with a drug and a bending portion formed between the first and second main strut portions. The method includes a drug coating process of coating the stent with the drug. The drug coating process includes a non-coating portion forming process including coating an outer surface of the first main strut portion with the drug by causing a nozzle for discharging a coating solution prepared by dissolving the drug and a polymer in a solvent to move along the first main strut portion, and when the nozzle reaches the bending portion, preventing the bending portion from being coated with the drug by causing the nozzle to go past over the bending portion and to move toward the second main strut portion. In the non-coating portion forming process, an adhesion amount of the coating solution adhering to the nozzle is reduced while the nozzle is going past the bending portion.

According to the present disclosure, a drug coating layer is not formed in a bending portion (portion where stress concentration or distortion occurs due to expanding deformation) of a strut in a manufactured stent. Accordingly, the stress concentration or the distortion can be prevented from occurring in the drug coating layer. In addition, when a nozzle unit passes through the bending portion, an adhesion amount of a coating solution adhering to (stored in) a nozzle can be reduced. Accordingly, a portion other than an outer surface of a main strut portion can be suitably prevented from being coated with a drug. Therefore, a manufacturing method of the stent can be provided, which prevents the drug from being peeled off or separated due to the stress concentration or the distortion resulting from the expanding deformation of the stent so that the drug is further uniformly effective and further improved yields are expected when the stent is manufactured.

BRIEF DESCRIPTION OF THE DRAWINGS

FIGS. 19A and 19B are partially enlarged views for describing a coating device according to a third embodiment of the present disclosure, wherein FIG. 19A illustrates a coating device including a cleaning portion, and FIG. 19B illustrates a coating device including a cleaning portion according to a modification example.

FIGS. 20A and 20B are partially enlarged views for describing a coating device according to a fourth embodiment of the present disclosure, wherein FIG. 20A illustrates a coating device including a collecting portion, and FIG. 20B illustrates a coating device including a suctioning and discharging portion.

DETAILED DESCRIPTION

Hereinafter, embodiments according to the present disclosure will be described with reference to the drawings.

Figure 1:
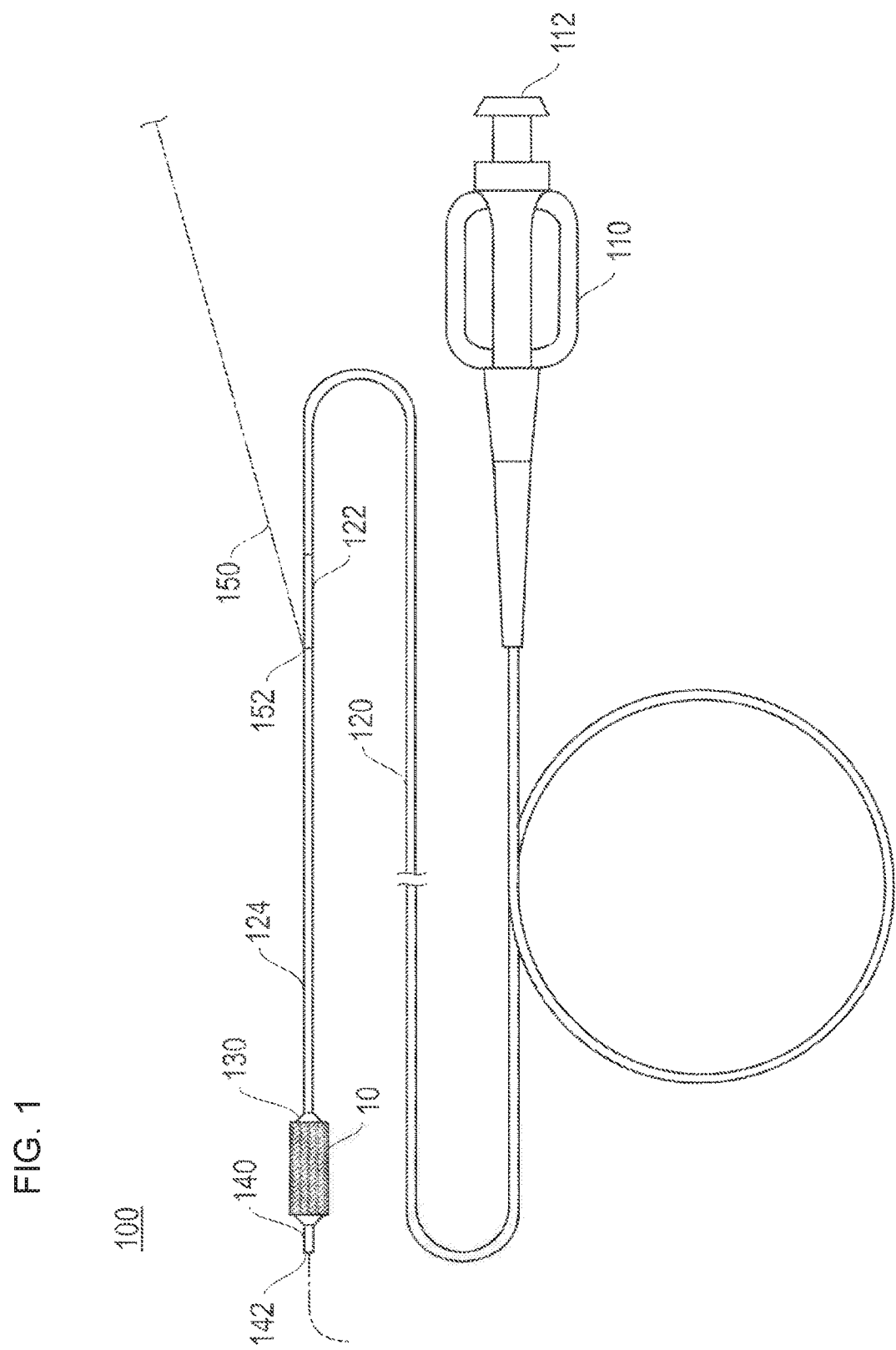
FIG. 1 is a schematic view for describing a stent delivery system to which a stent according to an embodiment of the present disclosure is applied.

FIG. 1 is a schematic view for describing a stent delivery system to which a stent according to an embodiment of the present disclosure is applied.

A stent 10 according to the embodiment of the present disclosure can include a drug eluting stent (DES) whose outer surface is coated with a drug, and has a function as a living body indwelling device which secures a lumen by indwelling the lumen after coming into close contact with an inner surface of a stenosed portion. For example, the stent 10 is applied to a stent delivery system 100 illustrated in FIG. 1, and is utilized for treatment which aims to prevent restenosis after percutaneous transluminal coronary angioplasty (PTCA, PCI).

The stent delivery system 100 can be a rapid exchange (RX) type which has a structure in which a guide wire 150 passes through only a distal portion, and has a hub 110, a proximal shaft 120, an intermediate shaft 122, a distal shaft 124, a balloon 130, and an inner tube shaft 140 in addition to the stent 10.

The hub 110 has an opening portion 112 having a lure taper formed in order to connect an auxiliary device, and is joined to the proximal shaft 120 while a liquid-tight state is maintained. For example, the auxiliary device is an indeflator (pressure applying device) for supplying a balloon dilation fluid. The balloon dilation fluid can include water, a physiological salt solution, or an electrolytic solution.

The proximal shaft 120 has a lumen which communicates with the opening portion 112 of the hub 110, and is joined to the intermediate shaft 122 while a liquid-tight state is maintained. The intermediate shaft 122 has a lumen, which communicates with the lumen of the proximal shaft 120, and is joined to the distal shaft 124 while a liquid-tight state is maintained. The distal shaft 124 has a lumen which communicates with the lumen of the intermediate shaft 122, and is connected to the balloon 130 while a liquid-tight state is maintained. A guide wire port 152 for internally introducing the guide wire 150 is disposed in a boundary between the intermediate shaft 122 and the distal shaft 124.

The balloon 130 has the stent 10 arranged on the outer periphery, and communicates with the lumen of the distal shaft 124. The balloon 130 is arranged in a folded state (or in a deflated state) so as to be dilatable, and the lumen of the distal shaft 124 communicates with the opening portion 112 of the hub 110 by way of the lumen of the intermediate shaft 122 and the lumen of the proximal shaft 120. Therefore, the balloon dilation fluid introduced from the opening portion 112 of the hub 110 can reach the inside of the balloon 130. That is, the balloon dilation fluid is introduced into the balloon 130 so as to dilate the balloon 130. In this manner, the stent 10 arranged on the outer periphery of the balloon 130 can expand so as to increase the diameter.

The inner tube shaft 140 is introduced into the distal shaft 124 from the boundary between the distal shaft 124 and the intermediate shaft 122, while a liquid-tight state is maintained. The inner tube shaft 140 penetrates the lumen of the distal shaft 124 and the balloon. The distal portion protrudes beyond the balloon 130 while a liquid-tight state is maintained. The inner tube shaft 140 has a lumen which causes the guide wire port 152 and an opening portion 142 located on a distal portion end surface to communicate with each other. The lumen is used in order to insert the guide wire 150.

For example, the stent 10 is caused to indwell as follows by the stent delivery system 100.

First, a distal portion of the stent delivery system 100 is inserted into a lumen of a patient, and is positioned at a targeted stenosed portion while the guide wire 150 protruding beyond the opening portion 142 of the inner tube shaft 140 is moved ahead. Then, the balloon dilation fluid is introduced from the opening portion 112 of the hub 110 so as to dilate the balloon 130. The stent 10 is subjected to expansion and plastic deformation, and is brought into close contact with the stenosed site.

Thereafter, the balloon 130 is decompressed and deflated. In this manner, the stent 10 and the balloon 130 disengage from each other so as to separate the stent 10 from the balloon 130. In this way, the stent 10 is caused to indwell the stenosed portion. Then, the stent delivery system 100 separated from the stent 10 is moved rearward, and is removed from the lumen.

Next, configuration materials of each unit will be described.

The stent 10 is configured to include a biocompatible material. For example, the biocompatible material can include iron, titanium, aluminum, tin, tantalum, a tantalum alloy, platinum, a platinum alloy, gold, a gold alloy, a titanium alloy, a nickel-titanium alloy, a cobalt-based alloy, a cobalt-chromium alloy, stainless steel, a zinc-tungsten alloy, or a niobium alloy.

For example, the drug (biologically active substance) for coating the outer surface of the stent 10 is at least one compound selected from a group including anticancer drugs, immunosuppressive drugs, antibiotics, anti-rheumatic drugs, anti-thrombotic drugs, HMG-CoA reductase inhibitors, ACE inhibitors, calcium antagonists, anti-hyperlipidemic drugs, integrin inhibitors, anti-allergic drugs, anti-oxidants, GP IIb/IIIa antagonists, retinoids, flavonoids, carotenoids, lipid improving drugs, DNA synthesis inhibitors, tyrosine kinase inhibitors, antiplatelet drugs, anti-inflammatory drugs, biologically-derived materials, interferon, and nitric oxide production-promoting substances.

For example, the configuration material of the hub 110 can include thermoplastic resins such as polycarbonate, polyamide, polysulfone, polyacrylate, and methacrylate-butylene-styrene copolymer.

For example, the configuration material of the proximal shaft 120 can include relatively strong rigid metal materials such as stainless steel, a stainless extensible alloy, a Ni—Ti alloy, brass, and aluminum. For example, if necessary, relatively strong rigid resin materials such as polyimide, vinyl chloride, and polycarbonate are also applicable.

The outer diameter of the proximal shaft 120 is, for example, 0.3 mm to 3 mm, and preferably 0.5 mm to 1.5 mm. The wall thickness of the proximal shaft 120 is, for example, 10 μm to 150 μm, and preferably 20 μm to 100 μm. The length of the proximal shaft 120 is, for example, 300 mm to 2,000 mm, and preferably 700 mm to 1,500 mm.

For example, the configuration material of the intermediate shaft 122 and the distal shaft 124 can include a polymer material such as polyolefin, cross-linked polyolefin, polyvinyl chloride, polyamide, polyamide elastomer, polyester, polyester elastomer, polyurethane, polyurethane elastomer, fluororesin, and polyimide, or a mixture of these materials. For example, polyolefin is polyethylene, polypropylene, polybutene, ethylene-propylene copolymer, ethylene-vinyl acetate copolymer, ionomer, or a mixture of two or more of these materials.

The outer diameter of the distal shaft 124 and the intermediate shaft 122 is, for example, 0.5 mm to 1.5 mm, and more preferably 0.7 mm to 1.1 mm. The wall thickness of the distal shaft 124 and the intermediate shaft 122 is, for example, 25 μm to 200 μm, and more preferably 50 μm to 100 μm. The length of the distal shaft 124 and the intermediate shaft 122 is, for example, 300 mm to 2,000 mm, and more preferably 300 mm to 1,500 mm.

For example, the configuration material of the balloon 130 is preferably a flexible material including a polymer material such as polyolefin, cross-linked polyolefin, polyester, polyester elastomer, polyvinyl chloride, polyurethane, polyurethane elastomer, polyphenylene sulfide, polyamide, polyamide elastomer, and fluororesin, or silicone rubber, and latex rubber. For example, polyester is polyethylene terephthalate. The configuration material of the balloon 130 is not limited to a form of utilizing the above-described polymer material alone. For example, it is also possible to apply a film on which the above-described polymer material is appropriately laminated.

The outer diameter of a cylindrical portion of the balloon 130 in case of being dilated is set to, for example, 1.0 mm to 10 mm, and preferably 1.0 mm to 5.0 mm. The individual length of the balloon 130 is, for example, 5 mm to 50 mm, and preferably 10 mm to 40 mm. The entire length of the balloon 130 is, for example, 10 mm to 70 mm, and preferably 15 mm to 60 mm.

For example, the configuration material of the inner tube shaft 140 is preferably a flexible material including a polymer material such as polyolefin, cross-linked polyolefin, polyvinyl chloride, polyamide, polyamide elastomer, polyester, polyester elastomer, polyurethane, polyurethane elastomer, polyimide, and fluororesin, or a mixture of these materials.

The outer diameter of the inner tube shaft 140 is, for example, 0.1 mm to 1.0 mm, and preferably 0.3 mm to 0.7 mm. The wall thickness of the inner tube shaft 140 is, for example, 10 μm to 150 μm, and preferably 20 μm to 100 μm. The length of the inner tube shaft 140 is, for example, 100 mm to 2,000 mm, and preferably 200 mm to 1,500 mm.

Without being limited to the rapid exchange type, the stent delivery system is also applicable to an over-the-wire (OTW) type. In this case, since the guide wire has a structure which passes through a hand operation side from the distal end, the guide wire is satisfactorily replaced or operated. In addition, without being limited to a form applied to the stenosed portion appearing in coronary arteries of the heart, the stent delivery system is also applicable to the stenosed portion appearing in other blood vessels, biliary ducts, bronchial tubes, esophagi, and urethrae.

Next, the stent 10 will be described in detail.

Figure 2:
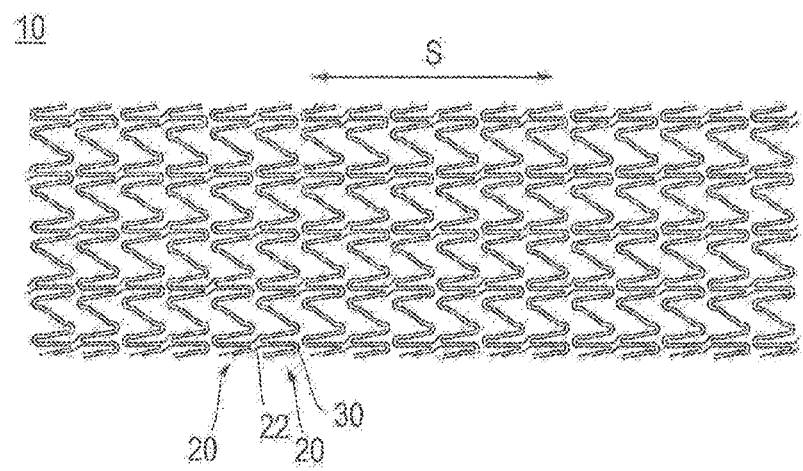
FIG. 2 is a plan view of the stent illustrated in FIG. 1.
Figure 3:
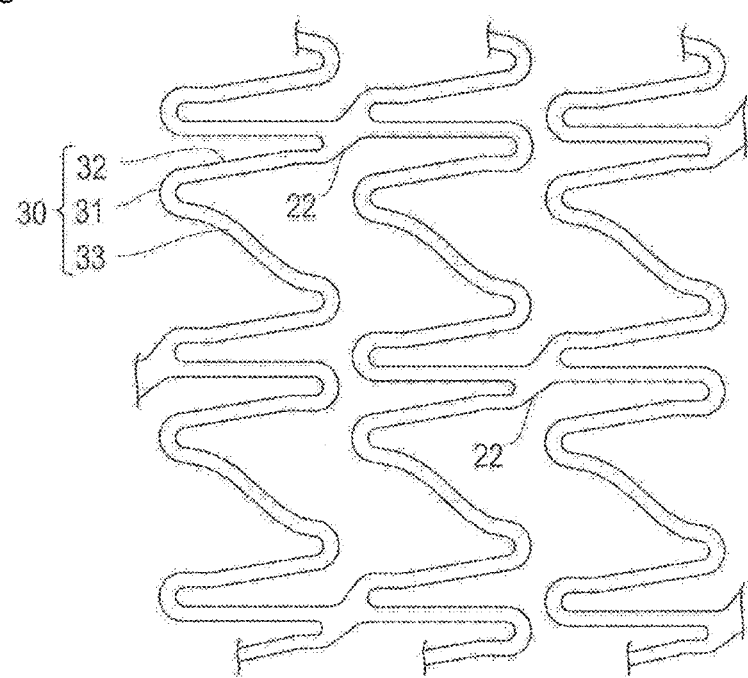
FIG. 3 is an enlarged view of the stent illustrated in FIG. 1.
Figure 4:
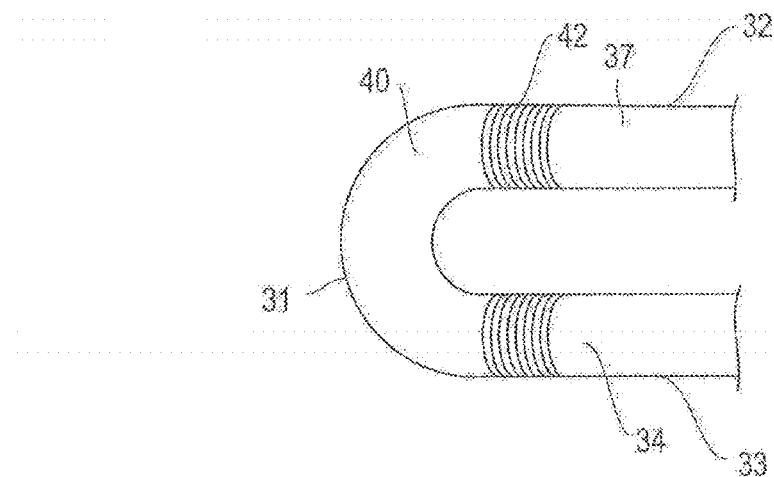
FIG. 4 is a plan view for describing a bending portion of a strut illustrated in FIG. 3.
Figure 5:
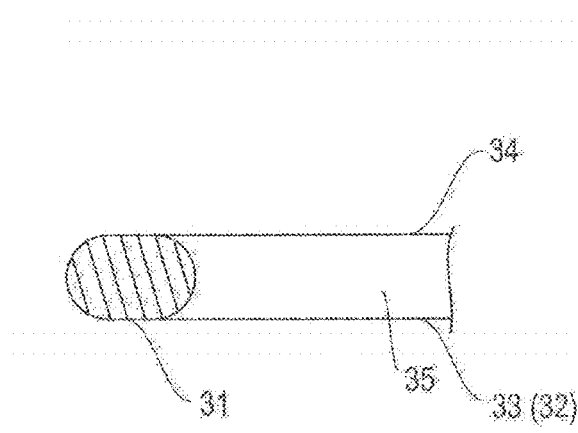
FIG. 5 is a cross-sectional view for describing the bending portion of the strut illustrated in FIG. 3.
Figure 6:
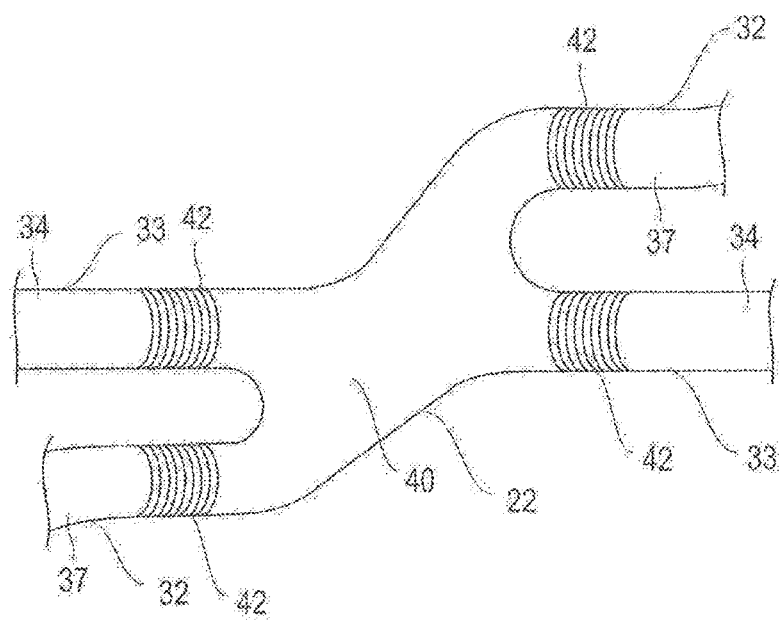
FIG. 6 is a plan view for describing a link portion of an annular body illustrated in FIG. 3.
Figure 7:
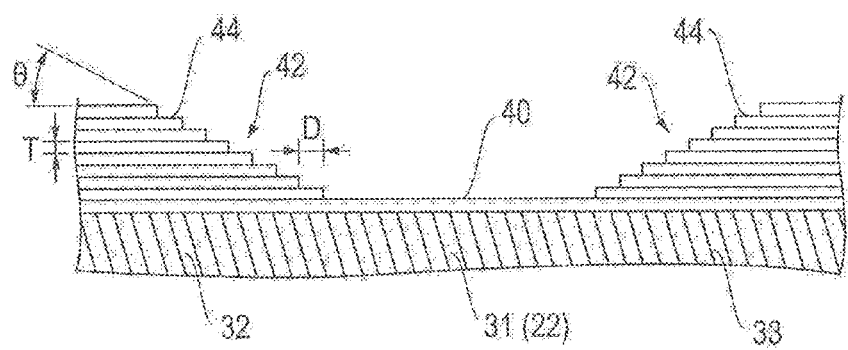
FIG. 7 is a cross-sectional view for describing a drug coating layer illustrated in FIGS. 4 to 6.

FIGS. 2 and 3 are respectively a plan view and an enlarged view of the stent illustrated in FIG. 1. FIGS. 4 and 5 are respectively a plan view and a cross-sectional view for describing a bending portion of a strut illustrated in FIG. 3. FIG. 6 is a plan view for describing a link portion of an annular body illustrated in FIG. 3. FIG. 7 is a cross-sectional view for describing a drug coating layer illustrated in FIGS. 4 to 6. In FIG. 7, the bending portion of the strut is linearly deformed in the illustration.

As illustrated in FIGS. 2 and 3, the stent 10 according to the embodiment of the present disclosure has an annular body 20 configured to include a strut 30. The strut 30 has main strut portions 32, 33 (corresponding to a first main strut portion and a second main strut portion) configured to be linear or curved, and multiple bending portions 31 formed between the respective main strut portions 32, 33. The strut 30 has a waved shape. The annular bodies 20 are sequentially juxtaposed along an axial direction S of the stent 10, and the adjacent annular bodies 20 are integrated with each other by the link portion 22. Therefore, a stent having a desired length can be easily obtained by increasing or decreasing the number of the annular bodies 20.

In accordance with an exemplary embodiment, it can be preferable that an area occupied by the strut 30 when the stent 10 does not expand in a state of being mounted on the balloon 130 is 60% to 80% of an outer peripheral area of the stent 10. The width of the strut 30 is preferably, for example, 40 μm to 150 μm, and more preferably 80 μm to 120 μm. The length of the main strut portions 32, 33 is preferably, for example, 0.5 mm to 2.0 mm, and more preferably 0.9 mm to 1.5 mm. The diameter of the stent 10 when the stent 10 does not expand is preferably, for example, 0.8 mm to 2.5 mm, and more preferably 0.9 mm to 2.0 mm. The length of the stent 10 when the stent 10 does not expand is preferably, for example, approximately 8 mm to 40 mm.

The drug for coating the outer surface of the stent 10 is loaded by a polymer so as to configure a drug coating layer 42. It is preferable that the polymer is a biodegradable polymer. In this case, after the stent 10 indwells a living body, the polymer is biodegraded, and the drug is gradually eluted. Accordingly, restenosis in a stent indwelling portion can be reliably prevented.

For example, the biodegradable polymer is at least one polymer selected from a group including polyester, aliphatic polyester, polyanhydrides, polyorthoester, polycarbonate, polyphosphazenes, polyphosphate ester, polyvinyl alcohol, polypeptides, polysaccharide, protein, and cellulose, a copolymer obtained by optionally copolymerizing a monomer configuring the above-described polymer, and a mixture of the polymers and/or the copolymers. For example, aliphatic polyester is polylactic acid (PLA), polyglycolic acid (PGA), or lactic acid-glycolic acid copolymer (PLGA).

As illustrated in FIGS. 4 to 6, the drug coating layer 42 is arranged on outer surfaces 34, 37 of the main strut portions 32, 33. That is, the bending portion 31 and the link portion 22 (portions where stress concentration and/or distortion occurs due to expanding deformation) of the strut 30 are not coated with the drug, and do not have the drug coating layer 42 formed thereon. Accordingly, the occurrence of the stress concentration and/or the distortion in the drug coating layer 42 can be avoided.

In addition, in the end portion of the main strut portions 32, 33 which is likely to receive the influence from the bending portion 31, only the outer surface 34 is coated with the drug, and the drug coating layer 42 is formed thereon. Accordingly, the drug coating layer 42 has improved peeling-off resistance. Since a non-drug coating portion (bending portion) is present, the uniform efficacy of the drug is less affected. Therefore, while the drug is satisfactorily and uniformly effective, the drug can be prevented from being peeled off or separated due to the stress concentration and/or the distortion resulting from the expanding deformation of the stent 10.

In accordance with an exemplary embodiment, a primer coating layer 40 can be arranged between the drug coating layer 42 and the outer surface of the stent 10. A primer configuring the primer coating layer 40 can be selected in view of adhesion to the polymer included in the drug coating layer 42 and adhesion to the outer surface of the stent 10. The presence of the primer coating layer 40 allows the drug coating layer 42 to have improved peeling-off resistance. If necessary, the primer coating layer 40 can also be omitted.

As illustrated in FIG. 7, the thickness of the drug coating layer 42 in the end portion of the main strut portions 32, 33 gradually decreases stepwise toward the bending portion 31 (and the link portion 22). Therefore, even in a case where the thickness of the drug coating layer 42 is increased, the thickness of the drug coating layer 42 located near the bending portion 31 and the link portion 22 can be thin. Thus, the occurrence of the stress concentration and/or the distortion caused by the increased thickness of the drug coating layer 42 can be minimized, and the drug can be prevented from being peeled off or separated. Accordingly, the required amount of the drug can be easily secured.

A tilting angle θ of the gradually decreased portion in the drug coating layer 42 is smaller than, for example, 90 degrees, preferably 1 degree to 60 degrees, and more preferably 1 degree to 45 degrees. For example, in a case where the tilting angle θ is smaller than, for example, 1 degree, an advantageous effect in preventing the drug removal is obtained over a wide range. Accordingly, the amount of the drug for coating is minimized. In addition, in a case where the tilting angle θ exceeds, for example, 60 degrees, there is a possibility that the advantageous effect in preventing the drug removal may no longer be expected.

As will be described later, the drug coating layer 42 is formed by being recoated with a coating solution prepared in such a way that the drug and the polymer are dissolved in a solvent. The length of a recoating layer 44 is sequentially changed, thereby gradually decreasing the thickness of the drug coating layer 42. A thickness T of the recoating layer 44 is preferably, for example, 1 μm to 5 μm. The thickness T of the recoating layer 44 is not limited to a form in which the thickness is always identical. The number of layers in the recoating layer 44 is preferably, for example, 2 to 50. A length difference D between the adjacent recoating layers 44 is preferably, for example, 1 μm to 1,000 μm. The length difference D is not limited to a form in which the length difference is always identical.

Next, a manufacturing method of the stent 10 will be described.

Figure 8:
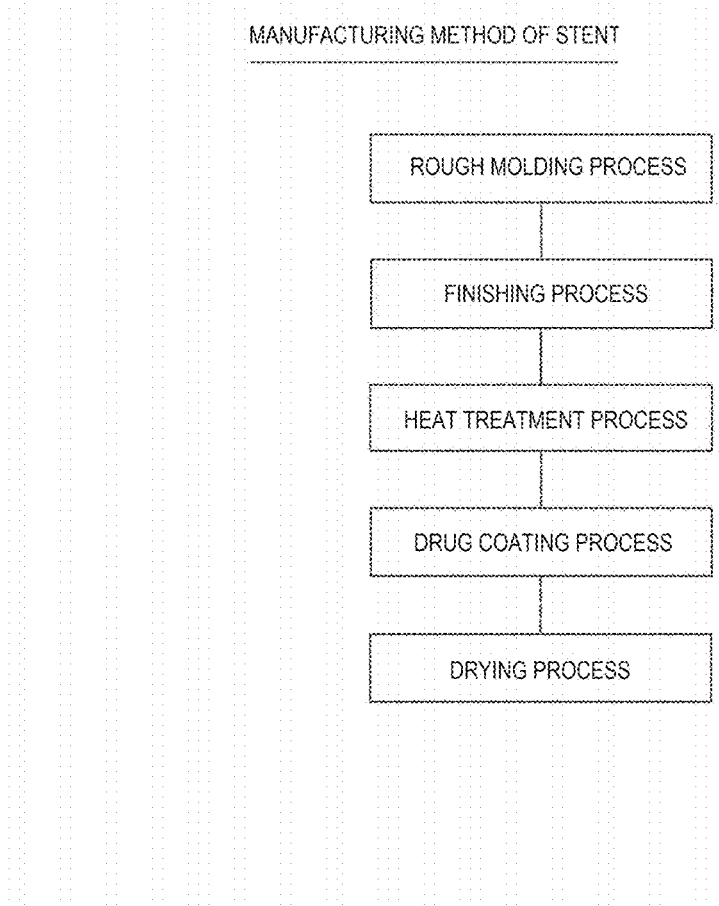
FIG. 8 is a flowchart for describing a manufacturing method of the stent illustrated in FIG. 1.

FIG. 8 is a flowchart for describing the manufacturing method of the stent illustrated in FIG. 1.

As illustrated in FIG. 8, the manufacturing method of the stent 10 has a rough molding process, a finishing process, a heat treatment process, a drug coating process, and a drying process.

In the rough molding process, a portion corresponding to a cavity portion of the stent is removed from a metal pipe body which is a stent material, thereby forming an annular body configured to include the strut and the link portion for integrating the adjacent annular bodies with each other. The portion corresponding to the cavity portion of the stent is removed by appropriately applying an etching method using masking and chemicals called photo-fabrication, an electrical discharge machining method using a mold, or a cutting method. For example, the cutting method is mechanical polishing or laser cutting.

For example, in the finishing process, an edge of the strut is removed by applying chemical polishing or electrolytic polishing, thereby finishing the strut so as to have a smooth surface.

In the heat treatment process, in order to improve the flexibility and bendability of the stent, annealing work is carried out, which helps enable the stent to satisfactorily indwell the curved blood vessel, and minimizes physical stimulation given to the intravascular wall. Accordingly, it is possible to reduce factors of restenosis. In the annealing work, it is preferable to gradually cool the stent after the stent is heated to, for example, 900° C. to 1,200° C. under an inert gas atmosphere so that an oxide film is not formed on the stent surface. For example, the inert gas is mixed gas between nitrogen and hydrogen. If necessary, the heat treatment process can also be appropriately omitted.

In the drug coating process, the stent is coated with the primer and the drug. Drug coating is performed on only the outer surfaces 34, 37 of the main strut portions 32, 33 except the bending portion 31 (refer to FIGS. 4 to 6). The drug is dissolved in a solvent together with the polymer, and is utilized in a form of the coating solution. For example, the solvent is acetone, ethanol, chloroform, or tetrahydrofuran.

In the drying process, the solvent is evaporated, and the drug coating layer 42 configured to include the drug and the polymer is formed, thereby manufacturing the stent 10.

In the manufactured stent 10, the bending portion 31 and the link portion 22 (portions where stress concentration and/or distortion occurs due to expanding deformation) of the strut 30 are not coated with the drug, and the drug coating layer 42 is not formed therein. Therefore, as described above, the drug is satisfactorily and uniformly effective, and the drug can be prevented from being peeled off or separated due to the stress concentration and/or the distortion resulting from the expanding deformation of the stent 10.

Next, a coating device applied to the drug coating process and the drug coating process will be sequentially described in detail.

Figure 9:
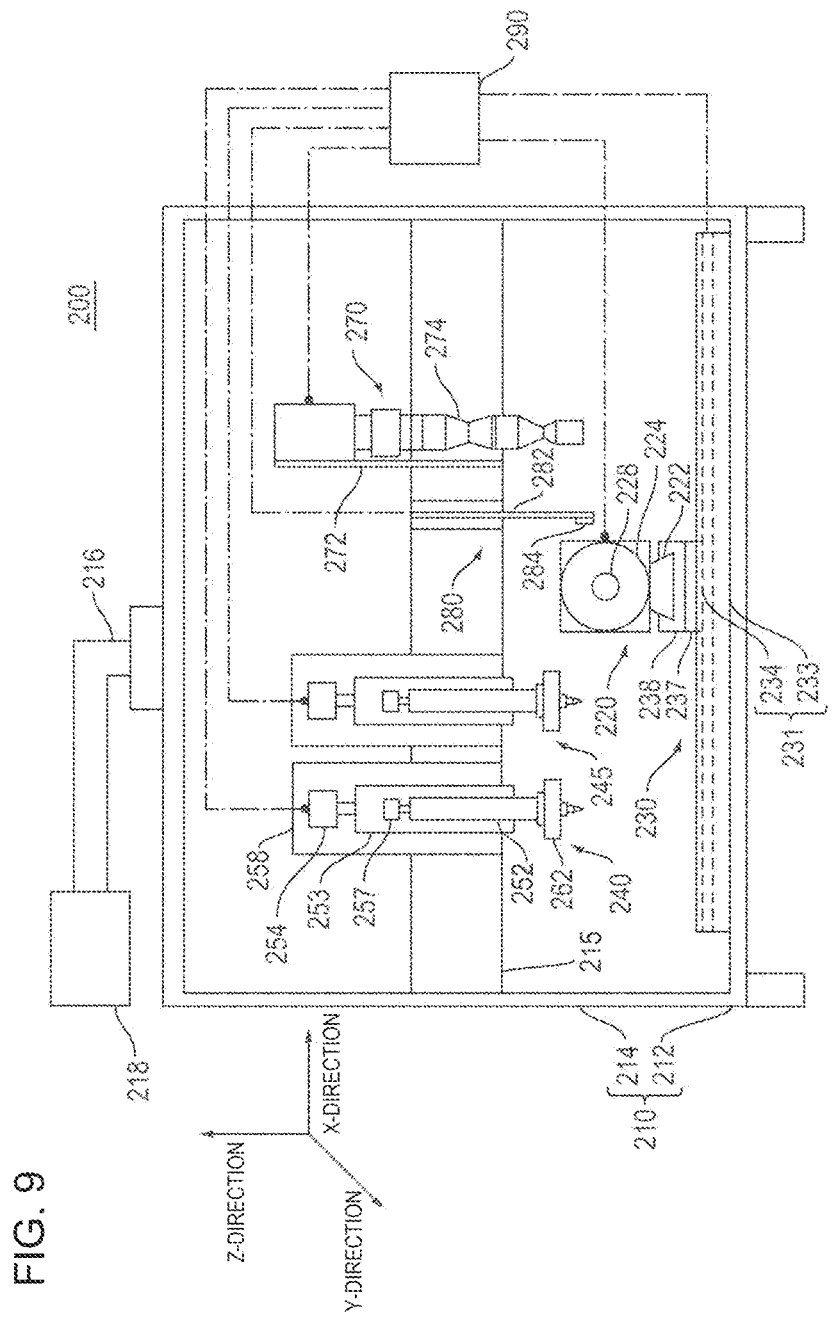
FIG. 9 is a front view for describing a coating device according to a first embodiment of the present disclosure.
Figure 10:
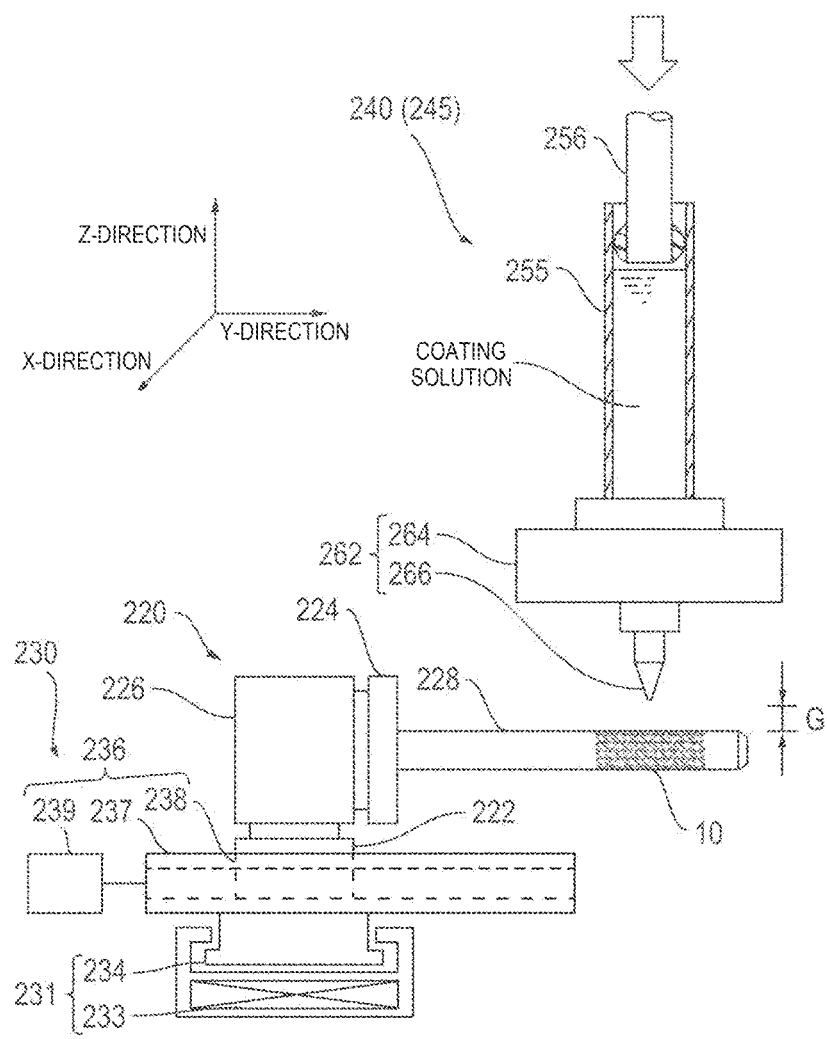
FIG. 10 is a side view of a main portion for describing the coating device according to the first embodiment of the present disclosure.
Figure 11:
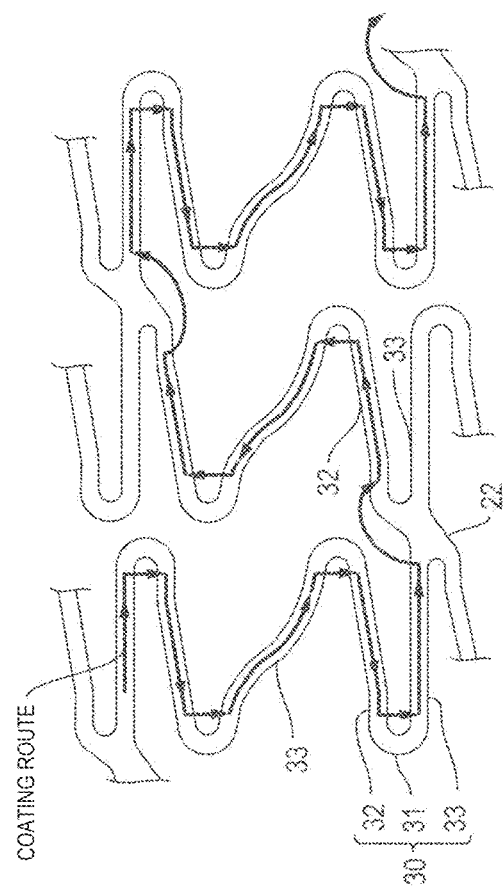
FIG. 11 is a plan view for describing a coating route of a nozzle in a second coating head.
Figure 12:
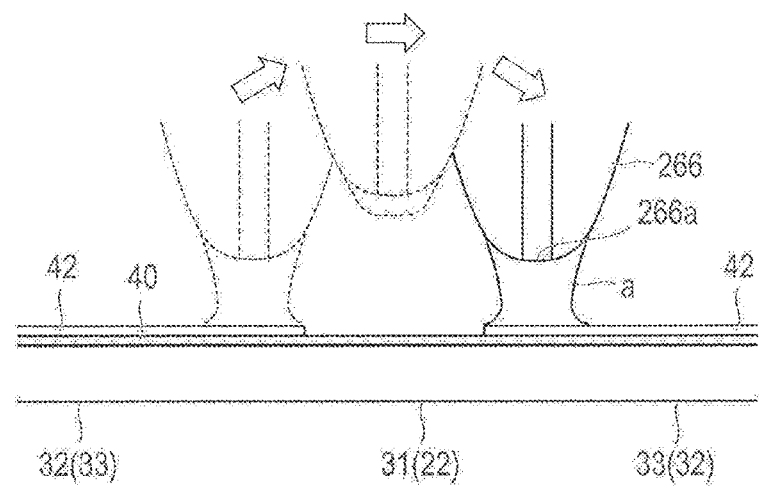
FIG. 12 is a side view for describing an operation of the nozzle in the second coating head.

FIGS. 9 and 10 are respectively a front view and a side view of a main section for describing the coating device applied to the drug coating process illustrated in FIG. 8. FIGS. 11 and 12 are respectively a plan view for describing a coating route of a nozzle in a coating head illustrated in FIG. 10, and a side view for describing an operation of the nozzle.

A coating device 200 has a chamber 210, a holding tool 220, a moving device 230, a first coating head 240, a second coating head 245, a first position information acquisition device 270, a second position information acquisition device 280, and a control unit 290.

The chamber 210 has a base 212, a main frame 214 arranged on the base 212, and a duct 216 interlocked to a top portion. The main frame 214 is covered with a transparent synthetic resin plate from the outer surface, and brings the inside of the chamber 210 into an air-tight state. An air conditioning device 218 is interlocked to the duct 216. The air conditioning device 218 supplies temperature and humidity-controlled air to the chamber 210. Therefore, coating conditions can be made constant by maintaining the inside of the chamber 210 in a state of constant temperature and humidity. The reference numeral 215 represents a support frame, which is laterally installed in the main frame 214.

The holding tool 220 is arranged at the bottom inside the chamber 210, is used in order to hold the stent 10, and has a base portion 222, a chucking portion 224, a motor 226, and a mandrel 228.

The base portion 222 is placed on the moving device 230, and is movable in an X-Y direction as will be described later. The chucking portion 224 and the motor 226 are arranged on the base portion 222. The chucking portion 224 is used in order to chuck the proximal end of the mandrel 228. The motor 226 is configured so that the chucking portion 224 can be rotated forward and rearward. The mandrel 228 has an outer periphery configured so that the stent 10 is attachable and detachable. Therefore, the holding tool 220 enables the stent 10 mounted on the mandrel 228 to rotate forward and rearward, and to move in an X-direction and a Y-direction.

In accordance with an exemplary embodiment, it is preferable that the outer diameter of the mandrel 228 is substantially equal to or slightly larger than the inner diameter of the stent 10. In order to increase a contrast ratio between the strut 30 and the cavity portion in the stent 10, it is preferable to coat the mandrel 228 with a black paint, which absorbs light. It is preferable that a concave portion for generating a gap between an outer peripheral surface of the mandrel 228 and a lower surface of the strut 30 of the stent 10 when the stent 10 is mounted on the mandrel 228 is formed on the outer peripheral surface of the mandrel 228. In this case, when the upper portion of the strut 30 is coated with the primer solution and the coating solution, the primer solution and the coating solution can be prevented from intruding into a portion between the surface of the mandrel 228 and the inner surface of the stent 10. Accordingly, the primer coating layer and the drug coating layer are allowed to have the uniform thickness, thereby improving convenience in the work. It is preferable that the mandrel 228 is replaceable. In this case, it is possible to deal with the stents 10 having various inner diameters by preparing the mandrels 228 having different outer diameter sizes.

The moving device (corresponding to moving means) 230 is used in order to move the holding tool 220 in the X-Y direction, and has an X-direction moving mechanism 231 and a Y-direction moving mechanism 236.

The X-direction moving mechanism 231 has a traveling rail 233 which extends in the X-direction and which has a linear motor-type drive source, and an X-direction moving table 234 which moves along the traveling rail 233. The Y-direction moving mechanism 236 has a traveling rail 237, which extends in the Y-direction, a Y-direction moving table 238 that moves along the traveling rail 237, and a motor 239 which drives the Y-direction moving table 238. The traveling rail 237 is placed on the X-direction moving table 234, and the base portion 222 of the holding tool 220 is placed on the Y-direction moving table 238.

The first coating head 240 is arranged in an intermediate portion inside the chamber 210, and is used in order to coat the coating solution prepared by dissolving the drug and the polymer in the solvent. The first coating head 240 has a dispenser 252, a vertical table 253, a bracket 258, and a nozzle unit 262 (refer to FIG. 10).

The dispenser 252 has a cylinder portion 255, a piston portion 256, and a drive unit 257, and is attached to the vertical table 253. The vertical table 253 is attached to the support frame 215 of the chamber 210 via the bracket 258, and is configured so that a screw feeding mechanism driven by the motor 254 enables the dispenser 252 to move in the Z-direction.

The cylinder portion 255 is a container for storing the coating solution, and is attached to the vertical table 253. The piston portion 256 is arranged inside the cylinder portion 255 so as to be slidable. For example, the drive unit 257 has a motor or a hydraulic pressure mechanism, and is configured to be capable of pressing the piston portion 256 by using a predetermined force.

The nozzle unit 262 communicates with the cylinder portion 255, and has an attachment member 264 and a nozzle 266. The attachment member 264 is arranged in a lower end of the cylinder portion 255, and is used in order to interlock the nozzle 266 to the cylinder portion 255.

The outer diameter of the distal end of the nozzle 266 is preferably, for example, 10 μm to 1,000 μm. The inner diameter (inner diameter of an opening portion 266a) of the distal end of the nozzle 266 is preferably, for example, 1 μm to 500 μm, and more preferably 5 μm to 250 μm. For example, in case where the inner diameter of the distal end of the nozzle 266 is smaller than, for example, 5 μm, the coating solution cannot smoothly flow out. In addition, great pressure is required to discharge the coating solution. In case where the inner diameter exceeds, for example 250 μm, there is a possibility that the coating solution cannot be smoothly used in the coating. In order to prevent the discharged coating solution from adhering to the inner surface of the nozzle 266, it is preferable to minimize the uneven surface by means of polishing.

The viscosity of the coating solution is preferably, for example, 0.1 cp to 10 cp, and more preferably 1.0 cp to 4.0 cp. For example, if the viscosity of the coating solution is higher than an upper limit of the above-described range, in some cases, discharge pressure of the coating solution becomes excessively high, or the coating solution cannot be discharged from the nozzle 266. In addition, if the viscosity is lower than a lower limit of the range, a portion of the discharged coating solution falls down from the surface of the stent 10 (strut 30). Consequently, it can be difficult to form a uniform coating layer.

In order to quantitatively discharge the coating solution under satisfactory control (in order to quantitatively, accurately, and reliably prepare the drug solution), a gap G between the nozzle 266 and the surface of the stent 10 (strut 30) is preferably 0.1 μm to 200 μm, and more preferably 1 μm to 100 μm. For example, if the gap G is larger than the upper limit of the range, there is a possibility that the discharging of the coating solution may be interrupted. If the gap G is smaller than the lower limit of the range, there is a possibility that the coating solution may fall down from the surface of the stent 10 (strut 30).

The second coating head 245 is arranged in the intermediate portion inside the chamber 210, and is used in order to perform coating of the primer solution. Except that the cylinder portion 255 stores the primer solution, the second coating head 245 is substantially the same as the first coating head 240, and thus, description thereof will be omitted.

The first position information acquisition device 270 is imaging means disposed in order to acquire a position information in the X-Y direction in the rectangular coordinate system on the surface of the stent 10 (strut 30), and is attached to the support frame 215 via the bracket 272. The first position information acquisition device 270 has a camera unit 274 and a line sensor unit arranged so as to extend in the axial direction of the stent 10. The line sensor unit is used in order to scan the surface of the stent 10 in synchronization with the rotation of the stent 10 attached to the mandrel 228 of the holding tool 220, in order to acquire image data on the surface of the stent 10, and in order to transmit the image data to the control unit 290.

The second position information acquisition device 280 is Z-direction displacement measurement means disposed in order to acquire a position information in the Z-direction in the rectangular coordinate system on the surface of the stent 10 (strut 30), is fixed to the lower end of the bracket 282 attached to the support frame 215, and has a laser displacement sensor 284. The laser displacement sensor 284 is a vertical sensor for measuring the Z-direction displacement of the strut 30, and is used in order to perform scanning along the trajectory passing through the center of the strut 30 while rotating the stent 10 forward and rearward, in order to acquire Z-direction displacement data of the entire stent 10, and in order to transmits the Z-direction displacement data to the control unit 290. Although not particularly limited, a measurement start point is set to a coating start position, for example.

The control unit 290 is arranged outside the chamber 210. For example, the control unit 290 has a microprocessor for controlling the above-described respective units or for performing various arithmetic processes in accordance with a program, a memory for storing various settings or data items, a monitor for displaying various settings or data items, and a keyboard for inputting various settings or data items. The control unit 290 is used in order to control the holding tool 220, the moving device 230, the first coating head 240, the second coating head 245, the first position information acquisition device 270, and the second position information acquisition device 280.

For example, the arithmetic processes are performed in order to acquire the X-Y direction position information, in order to acquire the Z-direction position information, and in order to set a coating route used by the nozzle 266.

In the process for acquiring the X-Y direction position information, based on the result that the strut 30 is brighter and the cavity portion is darker, image data on the surface of the stent 10 which is acquired from the first position information acquisition device 270 is binarized so as to have suitable brightness. In this manner, the image data is separated into the strut 30 and the cavity portion, then is converted into X-Y coordinates of the strut 30, that is, the X-Y direction position information in the rectangular coordinate system, and is stored in the memory. The obtained X-Y direction position information is used in order to calculate coordinates on the trajectory passing through the center of the strut 30, and the obtained coordinates of the trajectory are stored in the memory. When coating using the coating solution is performed, it is essential to perform the coating without being separated from the strut 30. Accordingly, it is important to identify the center of the strut 30.

In the process for acquiring the Z-direction position information, the Z-direction displacement data of the entire stent 10 which is acquired from the second position information acquisition device 280 is converted into the Z-direction position information in the rectangular coordinate system on the surface of the strut 30, and is stored in the memory. To be more exact, the strut 30 has no smooth surface, and has an uneven surface. Therefore, in order to quantitatively and accurately perform coating using the coating solution, based on the Z-direction position information, it is necessary to control the distal end of the nozzle 266 so as to move exactly parallel to the surface of the strut 30 and so as to perform the coating using a predetermined amount of the coating solution.

In the process for setting the coating route used by the nozzle 266, settings for performing continuous coating along the strut 30 are calculated by utilizing the X-Y direction position information and the Z-direction position information in the rectangular coordinate system of the strut 30 (the main strut portions 32, 33, the bending portion 31, and the link portion 22).

For example, as illustrated in FIG. 11, the coating route of the coating solution is set so as to continuously coat the main strut portions 32, 33 of the strut 30 with the coating solution and avoid the portions (the bending portion 31 and the link portion 22 of the strut 30) where stress concentration and/or distortion occurs due to expanding deformation.

The primer coating layer has a thin thickness, and has satisfactory peeling-off resistance with respect to the strut 30. Accordingly, the coating route of the primer solution is set so as to continuously coat the entire strut 30 with the primer solution.

In accordance with an exemplary embodiment, It can be preferable that the coating route has no overlapping section. However, in some cases, it is difficult to set the stent having the struts 30 complicatedly intersecting each other so as to have no overlapping section. In this case, moving speed in the overlapping section is caused to be faster than moving speed in no overlapping section. In this manner, it is possible to decrease a difference between the coating thickness in the overlapping section and the coating thickness in no overlapping section.

The movement along the coating route can be repeated multiple times. In this case, for example, the movement and the reverse movement along the coating route (reversing the movement directions) are alternately repeated, thereby increasing the thickness of the drug coating layer. Accordingly, the required amount of the drug can be easily secured.

Next, the drug coating process will be described in detail.

Figure 13:
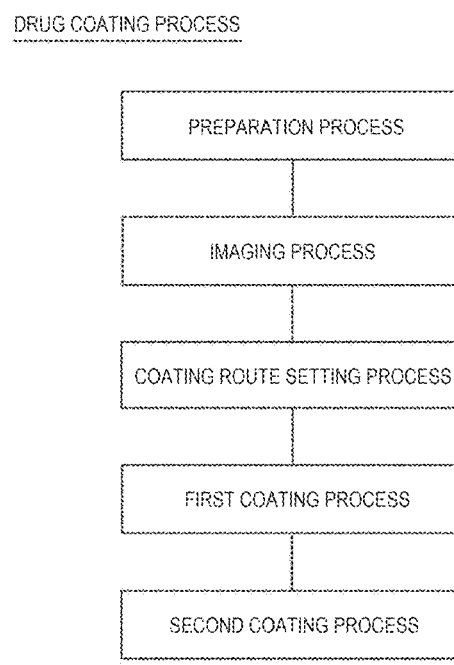
FIG. 13 is a flowchart for describing the drug coating process.

FIG. 13 is a flowchart for describing the drug coating process illustrated in FIG. 8. FIGS. 14, 15, 16, and 17 are respectively flowcharts for describing an imaging process, a coating route setting process, a first coating process, and a second coating process, which are illustrated in FIG. 13.

As illustrated in FIG. 13, the drug coating process has a preparation process, the imaging process, the coating route setting process, the first coating process, and the second coating process.

In the preparation process, the air conditioning device 218 is operated so as to bring the inside of the chamber 210 of the coating device 200 into a state of constant temperature and humidity. Then, the first coating head 240 and the second coating head 245 are attached to the support frame 215 of the chamber 210 via the vertical table 253 and the bracket 258. In addition, after being mounted on the mandrel 228, the stent 10 is positioned at a predetermined position by being attached to the chucking portion 224 of the holding tool 220 located at a standby position.

Figure 14:
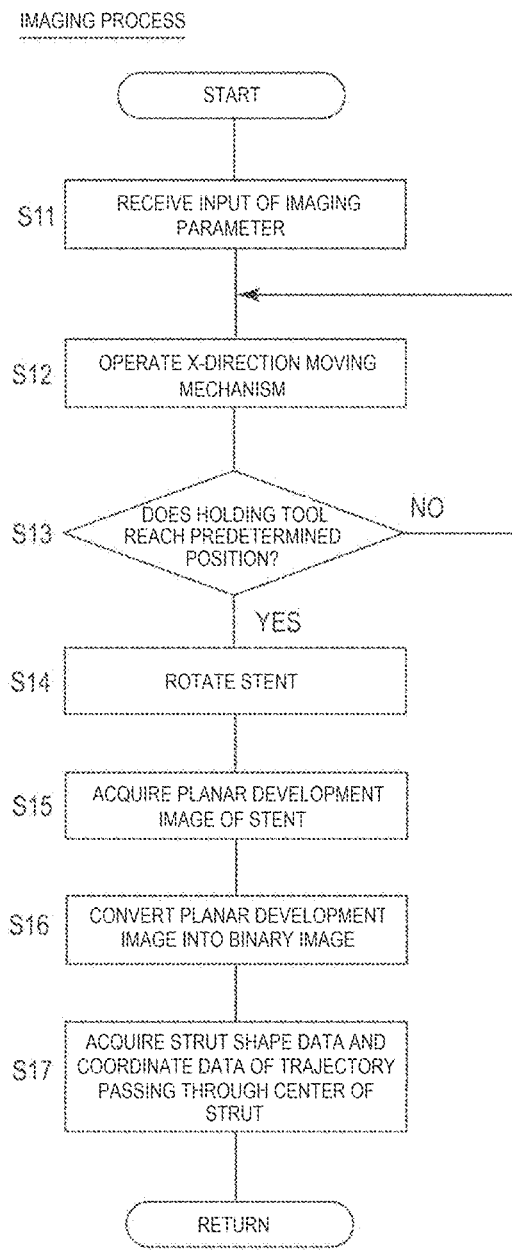
FIG. 14 is a flowchart for describing an imaging process illustrated in FIG. 13.

Next, the imaging process will be described with reference to FIG. 14.

First, the control unit 290 receives an input of an imaging parameter, and stores the input imaging parameter in the memory (Step S11). For example, the imaging parameter is input by an operator of the coating device 200 using a keyboard, and can include the rotation speed of the mandrel 228, the number of imaging lines obtained by the line sensor unit of the first position information acquisition device 270, the width of the imaging line, and the imaging speed.

The control unit 290 operates the X-direction moving mechanism 231 (Step S12). This causes the holding tool 220 to move along the traveling rail 233 from the standby position to a predetermined position below the first position information acquisition device 270. After confirming that the holding tool 220 reaches the predetermined position (Step S13: Yes), the control unit 290 operates the motor 226 of the holding tool 220, and rotates the mandrel 228 (stent 10) (Step S14).

The line sensor unit of the first position information acquisition device 270 scans the surface of the stent 10, and images surface patterns (Step S15). The scanned image is synthesized based on the imaging parameter, and is stored in the memory of the control unit 290 as a planar development image. If necessary, the planar development image can be output to a monitor so as to be visually confirmable.

The control unit 290 converts the planar development image of the stent 10 into a black and white binary image using a predetermined threshold value (Step S16), extracts an image of the strut 30, calculates shape data of the strut 30, and acquires coordinate data of the trajectory passing through the center of the strut 30 by performing a thinning process on the width of the strut 30 (Step S17).

Figure 15:
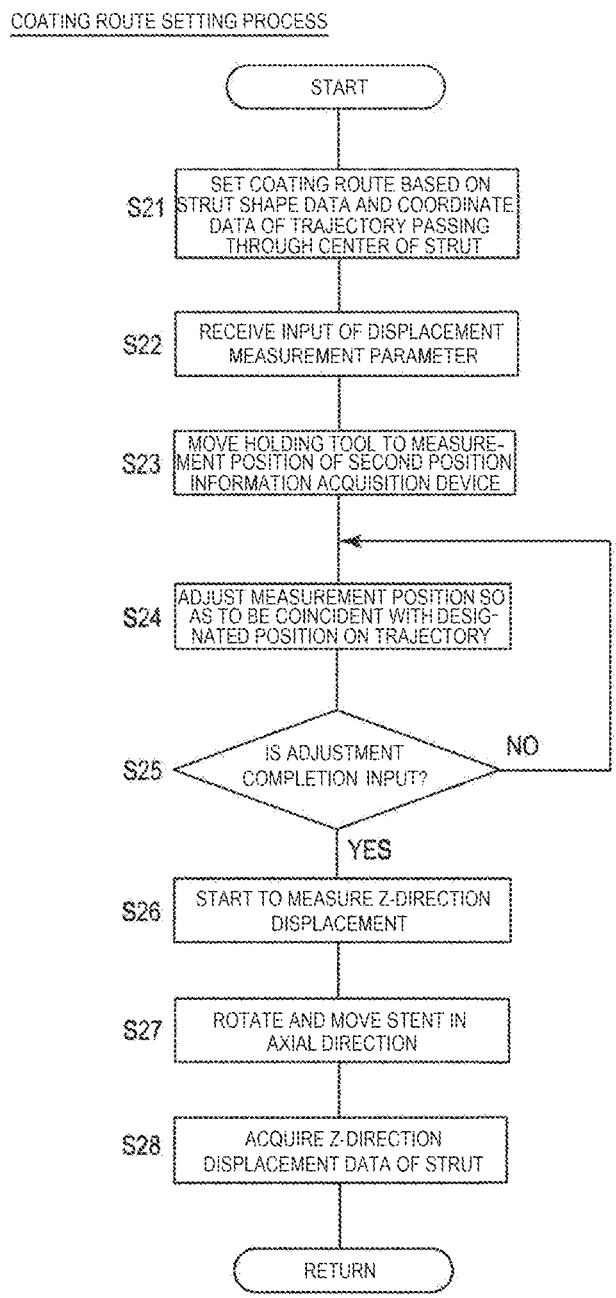
FIG. 15 is a flowchart for describing a coating route setting process illustrated in FIG. 13.

Next, the coating route setting process will be described with reference to FIG. 15.

Based on the acquired shape data of the strut 30 and the acquired coordinate data of the trajectory passing through the center of the strut 30, the control unit 290 sets the coating route in the first coating process and the coating route in the second coating process (Step S21). The coating route in the first coating process is generated so that the entire strut 30 can be continuously coated and the overlapping section can be minimized. The coating route in the second coating process is generated so as to avoid the portions (the bending portion 31 and the link portion 22 of the strut 30) where stress concentration and/or distortion occurs due to expanding deformation (refer to FIG. 11).

The control unit 290 receives an input of a displacement measurement parameter, and stores the input displacement measurement parameter in the memory (Step S22). For example, the displacement measurement parameter is input by the operator of the coating device 200 using the keyboard, and can include a measurement start position, a measurement direction, measurement speed, and a measurement interval, which are used by the second position information acquisition device 280.

The control unit 290 operates the motor 239 of the Y-direction moving mechanism 236, and moves the holding tool 220 (mandrel 228) to the measurement position to the second position information acquisition device 280 (Step S23). For example, the operator visually adjusts the stent 10 mounted on the mandrel 228 and the measurement position of the second position information acquisition device 280 so that the measurement position of the second position information acquisition device 280 is coincident with the designated position on the trajectory (Step S24).

For example, if the operator of the coating device 200 inputs adjustment completion by using the keyboard (Step S25: Yes), the control unit 290 commands the second position information acquisition device 280 to start measurement of the Z-direction displacement in the strut 30 (Step S26), causes the motor 226 to repeatedly rotate forward and rearward, and causes the motor 239 to repeatedly move in the axial direction. This causes the stent 10 to repeatedly rotate and move in the axial direction (Step S27).

The second position information acquisition device 280 moves along the trajectory passing through the center of the strut 30, acquires the Z-direction displacement data of the strut 30 of the entire stent 10, and transmits the Z-direction displacement data to the control unit 290 (Step S28). The Z-direction displacement data is converted into Z-direction position information in the rectangular coordinate system on the surface of the strut 30, and is stored in the memory together with the coordinates of the center trajectory.

Figure 16:
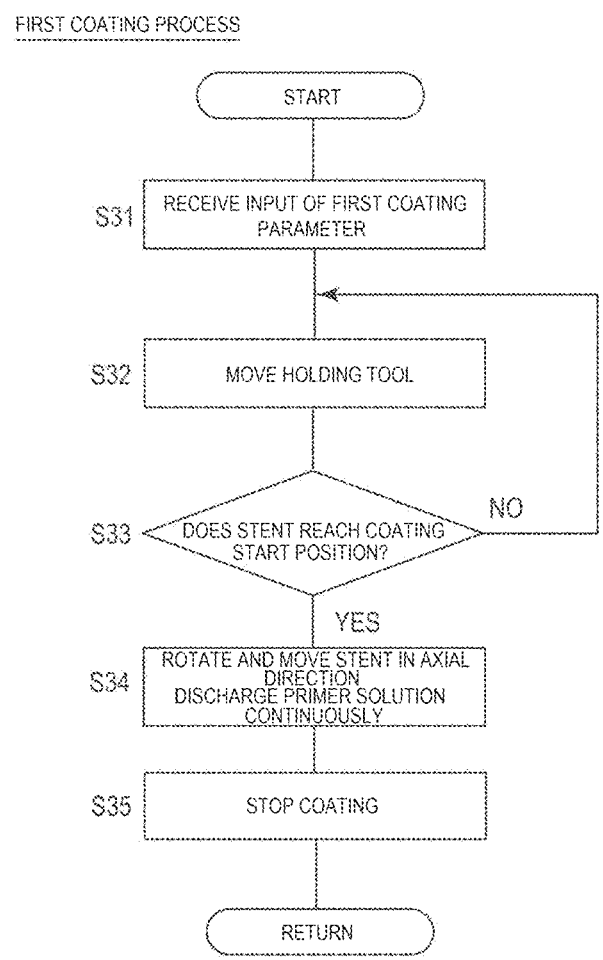
FIG. 16 is a flowchart for describing a first coating process illustrated in FIG. 13.

Next, the first coating process for forming the primer coating layer will be described with reference to FIG. 16.

The control unit 290 receives an input of a first coating parameter, and stores the input first coating parameter in the memory (Step S31). For example, the first coating parameter is input by the operator of the coating device 200 using the keyboard, and can include the rotation speed and the axial direction moving speed of the stent 10, selection of the second coating head 245, and the discharge speed of the second coating head 245 (nozzle unit 262).

The control unit 290 commands the X-direction moving mechanism 231 to move the holding tool 220 (Step S32). This causes the stent 10 mounted on the mandrel 228 of the holding tool 220 to move to the coating start position below the second coating head 245.

If the stent 10 reaches the coating start position (Step S33: Yes), the stent 10 is rotated and moved in the axial direction. The primer solution is continuously discharged from the nozzle unit 262 of the second coating head 245 (Step S34). At this time, the control unit 290 commands the motor 226 to rotate forward and rearward, and commands the motor 239 to move in the axial direction so as to move the stent 10 in the X-axis direction and the Y-axis direction, in accordance with the designated parameter. The control unit 290 commands the motor 254 to move the second coating head 245 in the Z-axis direction. Then, if the coating of the entire strut 30 is completed once along the predetermined coating route by the second coating head 245, the coating is stopped (Step S35).

As described above, in the first coating process, the outer surface of the strut 30 is coated with the primer (primer solution) before being coated with the drug. Accordingly, the drug coating layer is allowed to have improved peeling-off resistance. If necessary, the first coating process can also be omitted.

Figure 17:
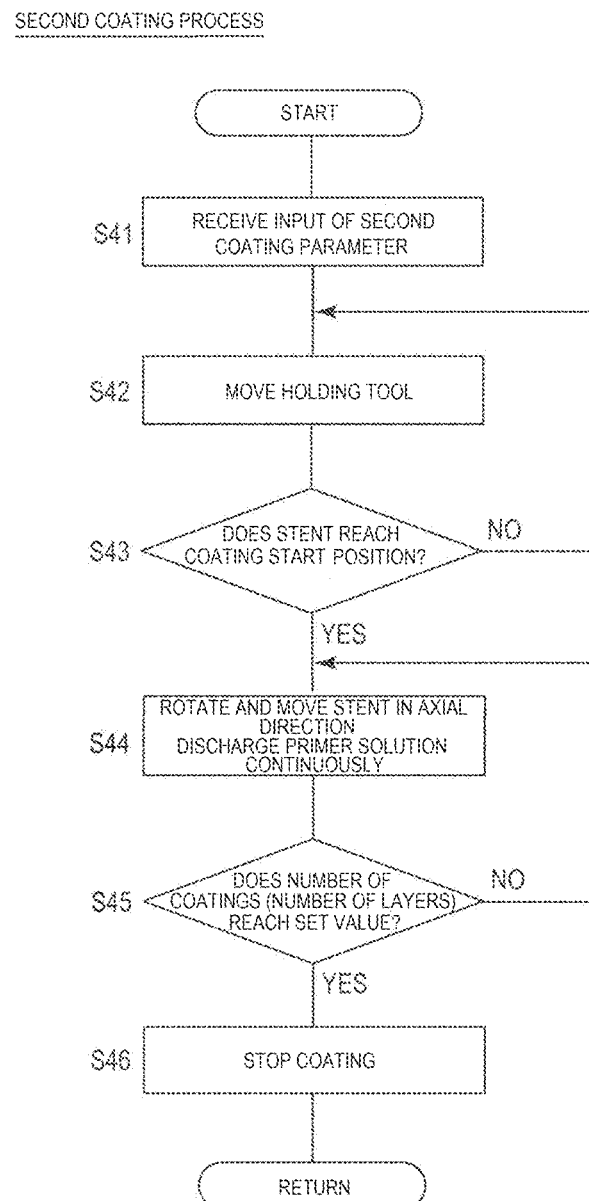
FIG. 17 is a flowchart for describing a second coating process illustrated in FIG. 13.

Next, the second coating process for forming the drug coating layer will be described with reference to FIG. 17.

The control unit 290 receives an input of a second coating parameter, and stores the input second coating parameter in the memory (Step S41). For example, the second coating parameter is input by the operator of the coating device 200 using the keyboard, and can include the rotation speed and the axial direction moving speed of the stent 10, selection of the first coating head 240, the discharge speed of the first coating head 240 (nozzle unit 262), and the number of coating processes (number of layers).

The control unit 290 commands the X-direction moving mechanism 231 to move the holding tool 220 (Step S42), which causes the stent 10 mounted on the mandrel 228 of the holding tool 220 to move to the coating start position below the first coating head 240.

If the stent 10 reaches the coating start position (Step S43: Yes), the stent 10 is rotated and moved in the axial direction, and the coating solution is continuously discharged from the nozzle unit 262 of the first coating head 240 (Step S44). At this time, the control unit 290 commands the motor 226 to rotate forward and rearward, and commands the motor 239 to move in the axial direction so as to move the stent 10 in the X-axis direction and the Y-axis direction, in accordance with the designated parameter. The control unit 290 commands the motor 254 to move the first coating head 240 in the Z-axis direction.

As a result, the first coating head 240 performs coating using the coating solution while moving along the predetermined coating route (refer to FIG. 11) in the second coating process. That is, the main strut portions 32, 33 of the strut 30 are continuously coated with the coating solution except the portions (the bending portion 31 and the link portion 22 of the strut 30) where stress concentration and/or distortion occurs due to expanding deformation.

In detail, in the second coating process, a non-coating portion forming process of preventing the bending portion 31 from being coated with the drug is performed in such a way that the outer surfaces 34,37 of the main strut portions 32, 33 are coated with the drug by causing the nozzle 266 for discharging the coating solution prepared by dissolving the drug and the polymer in the solvent to move along the main strut portions 32, 33, and that the nozzle 266 is caused to go past the bending portion 31 when the nozzle 266 reaches the bending portion 31 (or the link portion 22) and to move toward the main strut portion 33. The order for coating the respective main strut portions 32 and 33 with the drug may be the order of the main strut portion 33 and the main strut portion 32. Then, without being limited to the coating route (refer to FIG. 11) for performing the coating using the coating solution as described above, other coating routes can also be set.

Here, as illustrated in FIG. 12, when the nozzle 266 reaches the bending portion 31, the control unit 290 causes the nozzle 266 to perform separating movement (jumping) in the Z-axis direction, thereby preventing the bending portion 31 from being coated with the coating solution. Then, according to the present embodiment, an adhesion amount of the coating solution adhering to the nozzle 266 is reduced while the nozzle 266 is going past the bending portion 31. The reason is to prevent a case where the coating solution is stored in the nozzle 266 while the nozzle 266 moves in the bending portion 31, where the coating solution is excessively discharged immediately after the nozzle 266 passes through the bending portion 31, and where the side surface 35 of the stent 10 is coated with the coating solution. As a method of preventing the bending portion 31 (or the link portion 22) from being coated with the coating solution, in addition to the method of moving the nozzle 266 in the Z-axis direction, for example, the nozzle 266 may be caused to pass through the outside or the inside of the bending portion 31 (or the link portion 22). In addition, the coating work may be carried out by combining the movement of the nozzle 266 along the routes with the movement of the nozzle 266 in the Z-axis direction. The movement of the nozzle 266 in this way can more effectively prevent the bending portion 31 (or the link portion 22) from being coated with the coating solution.

As a method of reducing the adhesion amount of the coating solution, specifically, a method is employed in which a discharge amount of the coating solution from the nozzle 266 is changed while the nozzle 266 is going past the bending portion 31. The control unit 290 performs an operation for changing a discharge amount of the coating solution in synchronization with the timing when the nozzle 266 starts to move in the Z-axis direction. When the nozzle 266 is moved to the outside or the inside of the bending portion 31 or the link portion 22, the operation for changing the discharge amount of the coating solution is performed in synchronization with the timing when the nozzle 266 moves from the top of the strut 30.

For example, the above-described operation for "changing the discharge amount" can include an operation for stopping the discharge of the coating solution from the nozzle 266, an operation for suctioning or removing the coating solution adhering to the nozzle 266, and an operation for reducing an adhesion amount of the coating solution (to be described in the following embodiment). According to the present embodiment, the discharge amount is changed by performing the operation for stopping the discharge of the coating solution from the nozzle 266.

After the nozzle 266 goes past the bending portion 31, the discharge of the coating solution from the nozzle 266 is started in synchronization with the movement in the Z-axis direction in which the nozzle 266 moves close to the main strut portions 32, 33 again. In this way, when the nozzle 266 passes through the bending portion 31, the adhesion amount of the coating solution adhering to (stored in) the nozzle 266 can be reduced. Accordingly, a portion other than the outer surfaces 34, 37 of the main strut portions 32, 33 can be prevented from being coated with the drug. In a case where the nozzle 266 is moved to the outside or the inside of the bending portion 31 or the link portion 22, the discharge of the coating solution is started in synchronization with the timing when the nozzle 266 moves to the top of the strut 30.

Then, in the second coating process, if the number of coating processes (number of layers) reaches a set value by alternately repeating the movement and the reverse movement along the coating route (reversing the movement directions) (Step S45: Yes), the coating is stopped (Step S46). If the holding tool 220 is moved to the standby position by the X-direction moving mechanism 231, the mandrel 228 is detached from the holding tool 220. Then, the stent 10 (refer to FIG. 7) on which the primer coating layer 40 and the drug coating layer 42 are formed is detached from the mandrel 228.

In accordance with an exemplary embodiment, the movement directions of the nozzle unit 262 are alternately and repeatedly reversed, thereby performing recoating of the drug and increasing the thickness of the drug coating layer 42. Accordingly, the required amount of the drug can be easily secured.

When the moving directions of the nozzle unit 262 are alternately and repeatedly reversed, a position of the nozzle unit 262 when moving from the end portion of the main strut portions 32, 33 to the end portion of the other main strut portions 32, 33 is changed. In this manner, the thickness of the drug coating layer 42 in the end portion of the main strut portions 32, 33 can be caused to gradually decrease toward the bending portion 31 (and the link portion 22). In this case, it is possible to minimize the occurrence of stress concentration and/or distortion caused by the increased thickness of the drug coating layer 42, thereby preventing the drug from being peeled off or separated. In addition, the thickness is easily controlled, and satisfactory workability is achieved when the drug coating layer 42 whose thickness gradually decreases toward the bending portion 31 (and the link portion 22) is formed.

As described above, according to the present embodiment, the drug coating layer 42 is not formed in the bending portion 31 (portion where stress concentration and/or distortion occurs due to expanding deformation) of the strut 30 in the manufactured stent 10. Therefore, the stress concentration or the distortion can be prevented from occurring in the drug coating layer 42. In addition, when the nozzle 266 passes through the bending portion 31, the adhesion amount of the coating solution adhering to (stored in) the nozzle 266 can be reduced. Accordingly, a portion other than the outer surfaces 34, 37 of the main strut portions 32, 33 can be prevented from being coated with the drug. Therefore, it is possible to provide the manufacturing method of the stent which prevents the drug from being peeled off or separated due to the stress concentration or the distortion resulting from the expanding deformation of the stent 10 so that the drug is further uniformly effective and further improved yields are expected when the stent 10 is manufactured.

In addition, in the non-coating portion forming process, the discharge amount of the coating solution from the nozzle 266 is changed while the nozzle 266 is going past the bending portion 31. Accordingly, it is possible to suitably reduce the adhesion amount of the coating solution adhering to the nozzle 266 while the nozzle 266 is going past the bending portion 31.

In addition, a portion where the thickness of the drug coating layer 42 gradually decreases is formed therein. Accordingly, even if a starting point which deforms due to the expansion of the stent 10 is slightly displaced from the bending portion 31 of the strut 30, the occurrence of the stress concentration or the distortion is considerably minimized in the drug coating layer 42. Therefore, it is possible to suitably prevent the drug from being separated. Moreover, the gradually decreased portion has a less drug coating amount. Accordingly, the drug itself becomes likely to follow the deformation of the stent 10. In this regard, it is also possible to prevent the drug from being separated.

In addition, the main strut portions 32, 33 present on each periphery of the bending portion 31 and the link portion 22 can be prevented from being excessively coated with the coating solution. Accordingly, the drug can be further uniformly effective in the entire stent 10, and further improved yields can be expected when the stent 10 is manufactured.

Next, referring to FIG. 18, a manufacturing method of a stent and a coating device according to a second embodiment of the present disclosure will be described. The same reference numerals are given to the same members, and description thereof will be partially omitted.

In the manufacturing method of the stent according to the above-described first embodiment, the adhesion amount of the coating solution adhering to the nozzle 266 is reduced by changing the discharge amount of the coating solution from the nozzle 266 while the nozzle 266 is going past the bending portion 31 (or the link portion 22, hereinafter, referred to as the bending portion 31). On the other hand, in the manufacturing method of the stent according to the present embodiment, the adhesion amount of the coating solution is reduced by closing the nozzle 266 while the nozzle 266 is going past the bending portion 31.

Figure 18:
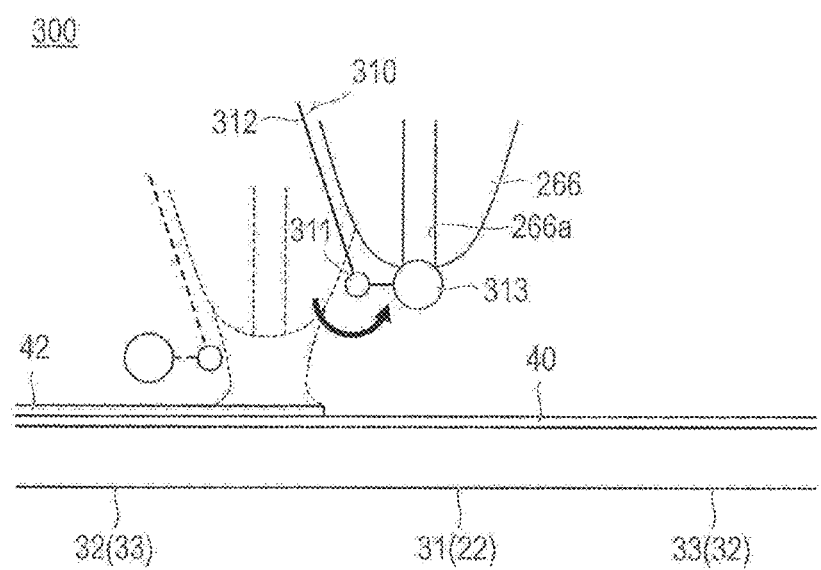
FIG. 18 is a partially enlarged view for describing a coating device according to a second embodiment of the present disclosure.

As illustrated in FIG. 18, a coating device 300 according to the present embodiment has coating solution reducing means 310 for reducing the adhesion amount of the coating solution. The coating solution reducing means 310 has an arm portion 312 in which a joint portion 311 is formed, and a nozzle closing portion 313 which is installed in a distal end of the arm portion 312.

If a predetermined control signal is issued from the control unit 290, the arm portion 312 performs a rotary operation (sliding operation) in the horizontal direction so as to press the nozzle closing portion 313 against an opening portion 266a of the nozzle 266. For example, this operation is performed in synchronization with the control signal issued when the nozzle 266 performs separating movement (jumping) from the bending portion 31 of the stent 10 after the nozzle 266 carries out work for coating the first main strut portion 32 with the coating solution. A broken line in the drawing indicates a state before the arm portion 312 is operated, and a solid line in the drawing indicates a state where the nozzle 266 is closed after the arm portion 312 is operated.

A shape of the nozzle closing portion 313 is not particularly limited as long as the nozzle 266 can be closed. However, for example, in a case where the nozzle closing portion 313 is formed in a spherical shape as illustrated, the nozzle closing portion 313 is pressed against the opening portion 266a of the nozzle 266 without any gap therebetween. Accordingly, the coating solution can be prevented from falling down from the nozzle 266. In addition, a material of the nozzle closing portion 313 is also not particularly limited since a known resin material or metal material can be used.

According to the manufacturing method of the stent and the coating device 300 in the present embodiment, since the nozzle 266 is closed, it is possible to suitably reduce the adhesion amount of the coating solution adhering to the nozzle 266 while the nozzle 266 is going past the bending portion 31. Accordingly, similarly to the method and the device according to the first embodiment, a portion other than the outer surfaces 34, 37 of the main strut portions 32, 33 can be prevented from being coated with the coating solution. Therefore, it is possible to more suitably improve yields when the stent is manufactured.

Next, referring to FIGS. 19A and 19B, a manufacturing method of a stent and a coating device according to a third embodiment of the present disclosure will be described. The same reference numerals are given to members which are the same as the members described in the respective embodiments, and description thereof will be partially omitted.

In the manufacturing method of the stent according to the above-described second embodiment, the nozzle 266 is closed while the nozzle 266 is going past the bending portion 31, thereby reducing the adhesion amount of the coating solution adhering to the nozzle 266. On the other hand, in the manufacturing method of the stent according to the present embodiment, the coating solution adhering to the nozzle 266 is removed while the nozzle 266 is going past the bending portion 31, thereby reducing the adhesion amount of the coating solution.

Figure 19A:
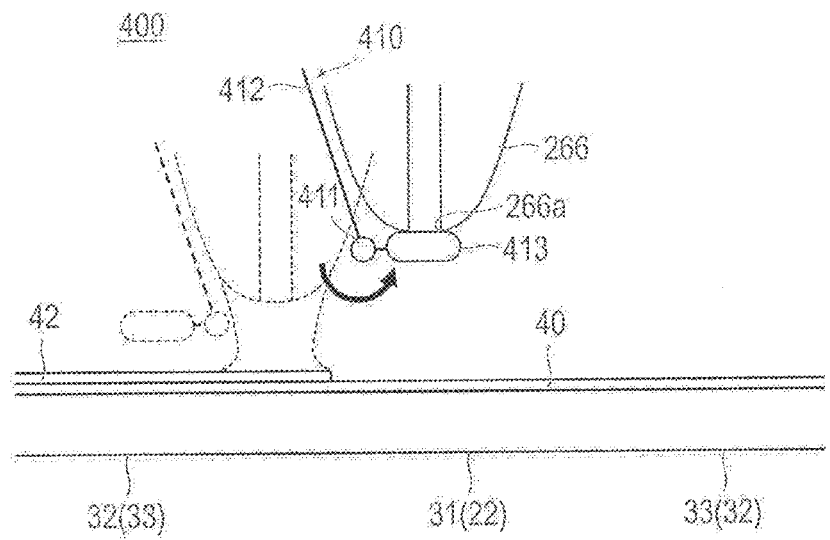

As illustrated in FIG. 19A, a coating device 400 according to the present embodiment has a coating solution removing portion 410 which removes the coating solution adhering to the nozzle 266, as the coating solution reducing means for reducing the adhesion amount of the coating solution. The coating solution removing portion 410 has an arm portion 412 on which a joint portion 411 is formed, and a cleaning portion 413 which is installed in a distal end of the arm portion 412.

For example, the arm portion 412 is operated so as to press the cleaning portion 413 installed in the distal end against the nozzle 266, in synchronization with a control signal issued when the nozzle 266 performs separating movement (jumping) from the bending portion 31 of the stent 10 after the nozzle 266 carries out work for coating the first main strut portion 32 with the coating solution.

For example, the cleaning portion 413 can be configured with a cloth impregnated with a cleaning agent such as acetone, ethanol, and cleaning water. In addition, for example, a configuration can also be adopted in which a cleaning agent supply portion (lumen) (not illustrated) is installed together so as to appropriately supply the cleaning agent to the cleaning portion 413.

Figure 19B:
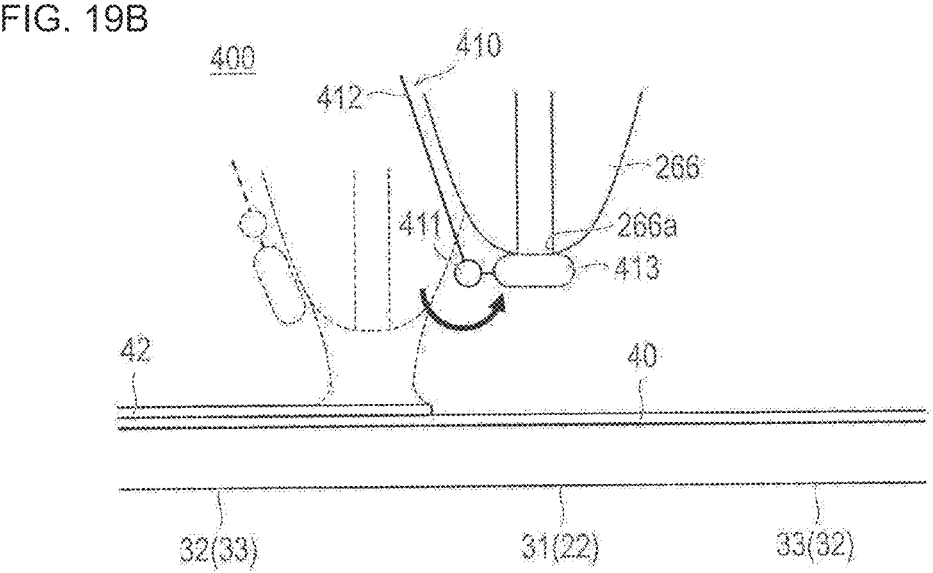

FIG. 19B illustrates a modification example of the coating solution removing portion 410.

As illustrated in FIG. 19B, a configuration of the arm portion 412 is not limited only to a configuration in which the cleaning portion 413 is operated so as to be pressed against the nozzle 266 by the rotary operation in the horizontal direction. For example, a configuration can also be adopted in which the cleaning portion 413 can move toward the distal end of the nozzle 266 along the outer surface of the nozzle 266. If this configuration is adopted, the coating solution can be removed over a relatively wide range in the distal end of the nozzle 266. Accordingly, it is possible to further improve yields of the coating solution. The operation of the arm portion 412 according to this modification example can also be applied to the arm portion 312 for operating the above-described nozzle closing portion 313.

According to the manufacturing method of the stent and the coating device 400 according to the present embodiment, since the nozzle 266 is cleaned, it is possible to suitably reduce the adhesion amount of the coating solution adhering to the nozzle 266 while the nozzle 266 is going past the bending portion 31. Accordingly, similarly to the method and the device according to the first embodiment and the second embodiment, a portion other than the outer surfaces 34, 37 of the main strut portions 32, 33 can be prevented from being coated with the coating solution. Therefore, it is possible to more suitably improve yields when the stent is manufactured. In addition, as illustrated in FIGS. 19A and 19B, if the size of the cleaning portion 413 is formed so as to be larger than the size of the distal end of the nozzle 266, the cleaning portion 413 can function as a closing portion. Accordingly, it is possible to more efficiently reduce the adhesion amount of the coating solution.

Next, referring to FIGS. 20A and 20B, a manufacturing method of a stent and a coating device according to a fourth embodiment of the present disclosure will be described. The same reference numerals are given to members which are the same as the members described in the respective embodiments, and description thereof will be partially omitted.

In the manufacturing method of the stent according to the above-described third embodiment, an embodiment of employing the cleaning portion 413 which cleans the nozzle 266 as the coating solution reducing means for reducing the adhesion amount of the coating solution has been described as an example. However, for example, the coating solution reducing means can also be configured to include a collecting portion 513 which collects the coating solution adhering to the nozzle 266.

Figure 20A:
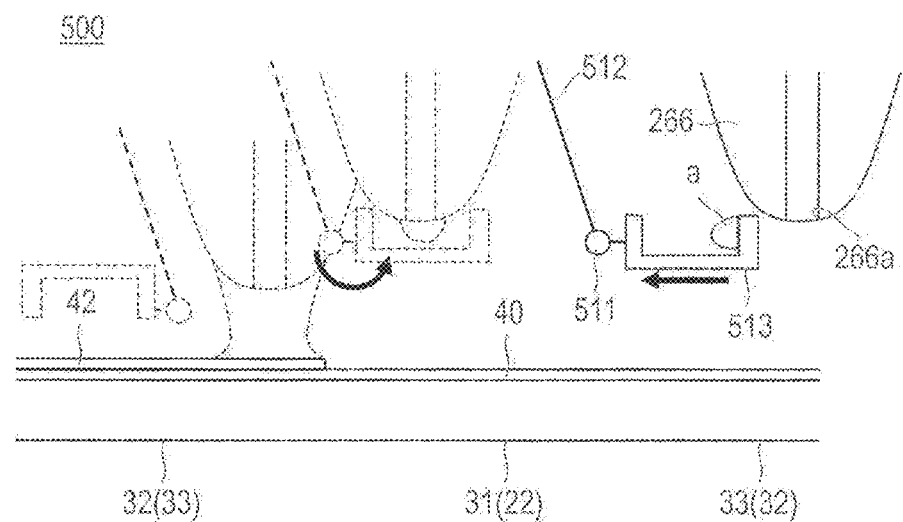

As illustrated in FIG. 20A, in a coating device 500 according to the present embodiment, the coating solution removing portion has an arm portion 512 in which a joint portion 511 is formed, and the collecting portion 513 which is installed in a distal end of the arm portion 512.

For example, the arm portion 512 is operated so as to cause the collecting portion 513 installed in the distal end to move close to the nozzle 266, in synchronization with a control signal issued when the nozzle 266 performs separating movement (jumping) from the bending portion 31 of the stent 10 after the nozzle 266 carries out work for coating the first main strut portion 32 with the coating solution. In addition, after the collecting portion 513 is moved close to a position where the coating solution can be collected, the collecting portion 513 is operated so as to rub a distal surface of the nozzle 266. This operation can suitably remove the coating solution adhering to the distal end of the nozzle 266.

For example, the collecting portion 513 can be formed in a substantially U-shape as illustrated. However, the shape is not particularly limited as long as the collecting portion 513 has a shape which can collect the coating solution. However, in a case where the collecting portion 513 is formed in a substantially U-shape, the coating solution can be collected so that the coating solution is caught on the collecting portion 513. Accordingly, it is possible to suitably remove the coating solution. A configuration material of the collecting portion 513 is not also particularly limited, and a known resin material or metal material can be used.

Figure 20B:
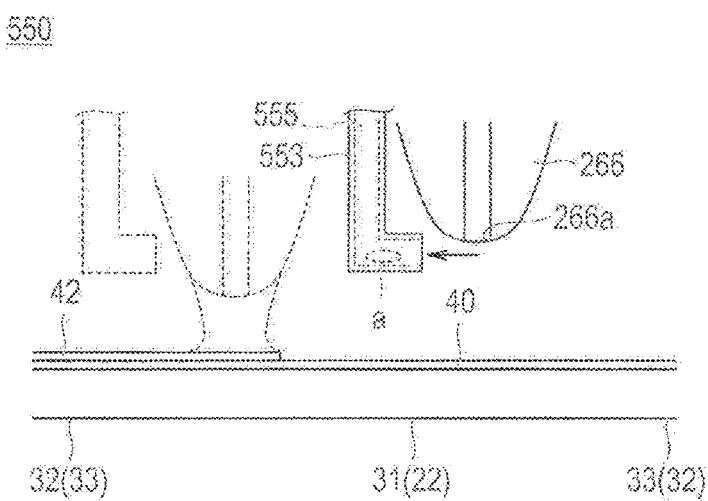

FIG. 20B illustrates a modification example of the coating solution removing portion. The coating solution removing portion according to this modification example has a suctioning and discharging portion 553 which can suction or discharge the coating solution. The suctioning and discharging portion 553 internally has a lumen 555 through which the coating solution can be passed. The suctioning and discharging portion 553 performs a suctioning operation or a discharging operation (fluid blowing) in synchronization with a control signal issued when the nozzle 266 performs separating movement (jumping) from the bending portion 31 of the stent 10. The coating solution is removed by the suctioning operation or the discharging operation of the suctioning and discharging portion 553. Accordingly, a portion other than the outer surfaces 34, 37 of the main strut portions 32, 33 can be prevented from being coated with the coating solution. Therefore, it is possible to more suitably improve yields when the stent is manufactured. As means for generating a suctioning force or a discharging force, for example, a known pump can be used.

Hitherto, various methods have been described as a method of reducing the coating amount of the coating solution adhering to the nozzle 266. However, the method according to the respective embodiments can be appropriately combined with each other. For example, in a state where a discharge amount of the coating solution from the nozzle 266 is changed, the nozzle 266 is closed, the nozzle 266 is cleaned, and the coating solution is removed. In this manner, it is possible to further reduce the amount of the coating solution stored in the nozzle 266.

In the method (device) according to the second to fourth embodiments, a procedure has been described in which the coating amount of the coating solution adhering to the nozzle is reduced in synchronization with (in line with) the jumping in the X-axis direction. However, as described in the first embodiment, the coating amount of the coating solution may be reduced in line with an operation in which the nozzle passes through the inside or the outside of the bending portion (or the link portion).

Furthermore, in the above-described respective embodiments, a case has been described where when the nozzle 266 is moved to the outside or the inside of the bending portion 31 or the link portion 22, or when the separating movement is performed, the discharge amount of the coating solution is changed (reduced or stopped, for example) in synchronization with the timing when the nozzle 266 moves from the top of the strut 30. However, an example is not necessarily limited to the case where the discharge amount is changed at the same timing when the movement is performed in synchronization therewith. For example, in a case where a period of time required for jumping in the X-axis direction is set to a time T, when the period of time is divided into four, the discharge amount of the coating solution may be changed during only a period of time starting from T/4 to 3T/4. That is, when the nozzle 266 is separated from the first main strut portion 32, the coating solution may be continuously supplied, the supply of the coating solution may be stopped while the nozzle 266 is going past the bending portion 31, and the supply of the coating solution may restart before the nozzle 266 reaches the second main strut portion 33. The discharge amount may be changed in conjunction therewith within a period of time while the jumping is performed, or may be changed in only the middle of jumping. If the supply of the coating solution is stopped concurrently with the jumping start or the supply of the coating solution restarts concurrently with the jumping end, coating work becomes irregular. Therefore, since the discharge amount is changed in only the middle of the jumping as described above, the coating work can be uniformly carried out on the strut 30 immediately before the jumping or after the jumping. Accordingly, it is possible to prevent the coating solution from spilling onto the side surface of the strut. Furthermore, depending on the viscosity of the coating solution, it is possible to obtain an advantageous effect of removing stringiness. In addition, the middle may be not only the intermediate time in terms of a time ratio as described above, but also the intermediate location in terms of a distance ratio.

Without being limited only to the above-described respective embodiments, the present disclosure can be modified in various ways within the scope described in Claims. For example, the first coating head storing a different coating solution in the cylinder portion may be installed at multiple locations. While the first coating heads are switched therebetween, the coating solution can also be used for recoating. In this case, according to a form in which the coating solution varies depending on the drug concentration, the drug concentration in the thickness direction of the drug coating layer is changed. In addition, according to a form in which the coating solution varies depending on a type of drugs, the type of drugs is changed in accordance with a position in the thickness direction of the drug coating layer. In this manner, it is possible to obtain composite efficacy.

The detailed description above describes a manufacturing method of a stent, and a coating device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A manufacturing method of a stent that has an annular body configured to include a waved strut which at least has first and second main strut portions to be coated with a drug and a bending portion formed between the first and second main strut portions, the method comprising:
    a drug coating process of coating the stent with the drug, wherein the drug coating process comprises a non-coating portion forming process including coating an outer surface of the first main strut portion with the drug by causing a nozzle for discharging a coating solution prepared by dissolving the drug and a polymer in a solvent to move along the first main strut portion, and when the nozzle reaches the bending portion, moving the nozzle in a separating movement in a Z-axis direction away from the stent and towards the second main strut portion, and thereby keeping the bending portion non-coated with the drug while the nozzle goes past the bending portion and moves to the second main strut portion; and
    wherein in the non-coating portion forming process, an adhesion amount of the coating solution adhering to the nozzle is reduced while the nozzle is going past the bending portion.

2. The manufacturing method of the stent according to claim 1,
    wherein in the non-coating portion forming process, changing a discharge amount of the coating solution from the nozzle while the nozzle is going past the bending portion.

3. The manufacturing method of the stent according to claim 1,
    wherein in the non-coating portion forming process, closing the nozzle while the nozzle is going past the bending portion by placing a nozzle closing portion against an opening portion of the nozzle.

4. The manufacturing method of the stent according to claim 1,
    wherein in the non-coating portion forming process, removing the coating solution adhering to the nozzle while the nozzle is going past the bending portion by collecting the coating solution, suctioning the coating solution, or discharging the coating solution.

5. The manufacturing method of the stent according to claim 1,
    wherein in the drug coating process, adjusting a thickness of a drug coating layer by discharging the coating solution from the nozzle while moving the nozzle along the strut so that the thickness of the drug coating layer of the first main strut portion and the second main strut portion gradually decreases toward the bending portion.

6. The manufacturing method of the stent according to claim 1, comprising:
    a plurality of the annular bodies juxtaposed along an axial direction of the stent;
    the strut further having a link portion for integrating the adjacent annular bodies with each other; and
    wherein in the drug coating process, a non-coating portion forming process of preventing the link portion from being coated with the drug is further performed by moving the nozzle to go past the link portion when the nozzle reaches the link portion, and reducing the adhesion amount of the coating solution adhering to the nozzle in the non-coating portion forming process.

7. The manufacturing method of the stent according to claim 1,
    wherein the coating solution is continuously supplied when the nozzle is separated from the first main strut portion, stopping the supply of the coating solution while the nozzle is going past the bending portion, and restarting the supply of the coating solution before the nozzle reaches the second main strut portion.

8. A coating device for coating, with a drug, a stent that has an annular body configured to include a waved strut which at least has first and second main strut portions to be coated with the drug and a bending portion formed between the first and second main strut portions, comprising:
- a holding tool configured to hold a stent;
- a nozzle that discharges a coating solution prepared by dissolving the drug and a polymer in a solvent;
- moving means for relatively moving the holding tool and the nozzle so that a predetermined portion of the stent is coated with the coating solution;
- a control unit that controls an operation of each unit in the coating device; and
- wherein an outer surface of the first main strut portion is coated with the drug by moving the nozzle along the first main strut portion, the bending portion is kept non-coated with the drug by causing the nozzle when the nozzle reaches the bending portion to move in separating movement in a Z-axis direction away from the stent and towards the second main strut portion, and reducing an adhesion amount of the coating solution adhering to the nozzle while the nozzle is going past the bending portion.

9. The coating device according to claim 8,
wherein the control unit changes a discharge amount of the coating solution from the nozzle while the nozzle is going past the bending portion.

10. The coating device according to claim 8, comprising:
coating solution reducing means for reducing the adhesion amount of the coating solution adhering to the nozzle.

11. The coating device according to claim 10,
wherein the coating solution reducing means has a nozzle closing portion which closes the nozzle.

12. The coating device according to claim 10,
wherein the coating solution reducing means has a coating solution removing portion which removes the coating solution adhering to the nozzle.

13. The coating device according to claim 12,
wherein the coating solution removing portion has at least one of a cleaning portion for cleaning the nozzle, a collecting portion for collecting the coating solution, and a suctioning and discharging portion for suctioning or discharging the coating solution.

14. The coating device according to claim 8, comprising:
- a plurality of the annular bodies juxtaposed along an axial direction of the stent;
- the strut further having a link portion for integrating the adjacent annular bodies with each other; and
- wherein the coating device prevents the link portion from being coated with the drug by moving the nozzle to go past the link portion when the nozzle reaches the link portion, and reduces the adhesion amount of the coating solution adhering to the nozzle while the nozzle is going past the link portion.

15. The coating device according to claim 8,
wherein the coating solution is continuously supplied when the nozzle is separated from the first main strut portion, the supply of the coating solution is stopped while the nozzle is going past the bending portion, and the supply of the coating solution restarts before the nozzle reaches the second main strut portion.

16. A manufacturing method of a stent that has an annular body configured to include a waved strut which at least has first and second main strut portions to be coated with a drug and a bending portion formed between the first and second main strut portions, the method comprising:
- coating an outer surface of the first main strut portion with the drug by causing a nozzle for discharging a coating solution prepared by dissolving the drug and a polymer in a solvent to move along the first main strut portion, and when the nozzle reaches the bending portion, preventing the bending portion from being coated with the drug by moving the nozzle in a separating movement in a Z-axis direction away from the stent and towards the second main strut portion; and
- reducing an adhesion amount of the coating solution adhering to the nozzle while the nozzle is going past the bending portion.

17. The manufacturing method of the stent according to claim 16, comprising:
changing a discharge amount of the coating solution from the nozzle while the nozzle is going past the bending portion.

18. The manufacturing method of the stent according to claim 16, comprising:
closing the nozzle while the nozzle is going past the bending portion by placing a nozzle closing portion against an opening portion of the nozzle.

19. The manufacturing method of the stent according to claim 16, comprising:
removing the coating solution adhering to the nozzle while the nozzle is going past the bending portion by collecting the coating solution, suctioning the coating solution, or discharging the coating solution.

20. The manufacturing method of the stent according to claim 16, comprising:
adjusting a thickness of a drug coating layer by discharging the coating solution from the nozzle while moving the nozzle along the strut so that the thickness of the drug coating layer of the first main strut portion and the second main strut portion gradually decreases toward the bending portion.

* * * * *